United States Patent [19]

Sakata et al.

[11] Patent Number: 5,308,772
[45] Date of Patent: May 3, 1994

[54] METHOD FOR CLASSIFYING AND COUNTING LEUKOCYTES

[75] Inventors: Takashi Sakata; Mitsue Ito, both of Hyogo, Japan

[73] Assignee: TOA Medical Electronics Co. Ltd., Japan

[21] Appl. No.: 903,238

[22] Filed: Jun. 23, 1992

[30] Foreign Application Priority Data

Jul. 29, 1991 [JP] Japan ................................ 2-188925

[51] Int. Cl.$^5$ ............................................ G01N 33/48
[52] U.S. Cl. ....................................... 436/63; 436/17; 436/172; 436/174; 436/800
[58] Field of Search ................... 436/17, 63, 172, 800, 436/166, 174

[56] References Cited

U.S. PATENT DOCUMENTS

| | | | |
|---|---|---|---|
| 3,906,120 | 9/1975 | Geating | 422/57 |
| 4,751,179 | 6/1988 | Ledis et al. | 436/63 |
| 5,039,613 | 8/1991 | Matsuda et al. | 436/17 |
| 5,122,453 | 6/1992 | Martin et al. | 436/172 |
| 5,175,109 | 12/1992 | Sakata et al. | 436/17 |

FOREIGN PATENT DOCUMENTS 0259833 3/1988 European Pat. Off. .

OTHER PUBLICATIONS

Frankel et al., "Gradwohl's Clinical Laboratory Method & Diagnosis", 1970, p. 508.

Primary Examiner—James C. Housel
Assistant Examiner—Lien Tran
Attorney, Agent, or Firm—Pearne, Gordon, McCoy & Granger

[57] ABSTRACT

A hematological specimen for classifying and counting leukocytes with a flow cytometer is prepared. A sample to be assayed is prepared by eliminating influences of erythrocytes from a hematological sample without changing leukocytes morphologically; adjusting the pH value to a level suitable for staining; and staining the leukocytes with at least two dyes including Astrazon Yellow 3G capable of specifically staining at least basophils and immature granulocytes and Neutral Red capable of specifically staining at least eosinophils. Thus leukocytes contained in the hematological sample can be classified at least three or six groups including immature granulocytes by measuring a single specimen with a flow cytometer.

7 Claims, 17 Drawing Sheets

FORWARD SCATTERED
LIGHT INTENSITY

SIDE SCATTERED
LIGHT INTENSITY

INTENSITY OF GREEN
FLUORESCENCE

INTENSITY OF RED
FLUORESCENCE

METHOD FOR CLASSIFYING AND COUNTING LEUKOCYTES

BACKGROUND OF THE INVENTION

1. Field of the Invention

The present invention relates to a process for preparing a specimen for classifying and counting blood corpuscles in the practice of clinical testing. More particularly, it relates to a method for preparing a specimen to be used in classifying and counting leukocytes with a flow cytometer by means of optical measurements on blood corpuscles.

2. Prior Art

Peripheral blood of normal subjects contains five types of leukocytes, namely, lymphocytes, monocytes, neutrophils, eosinophils and basophils.

These leukocytes differ from each other in function and, therefore, the classification and counting of leukocytes contained in the peripheral blood is highly useful in the diagnosis of various diseases.

It is well known that the peripheral blood of a patient with, for example, leukemia contains immature granulocytes which are usually observed not in the peripheral blood but in the bone marrow. Therefore, it is highly important to detect, classify and count these immature granulocytes for diagnostic purposes.

Classification and counting of leukocytes have most commonly been accomplished by the differential counting method which is also referred to as the visual counting method or simply as the manual method. In this method, a blood sample is smeared on a glass slide and the blood corpuscles in the smear are fixed and stained for microscopic examination. The technician identifies the type of individual leukocytes according to their morphological features or the degree of dye uptake and thus performs classification and counting. In ordinary laboratories, 100 to 200 leukocytes are usually counted for each sample and the percentage of the total leukocyte count occupied by each type of corpuscle is recorded as a measured value.

The differential counting method has several disadvantages such that the preparation of the specimen to be examined requires troublesome procedures; that the classification through microscopic observation should be made by a skilled person and the measured value considerably varies from technician to technician; that the small number of leukocytes to be counted causes large statistical errors; and that it is a great burden for the technician to classify and count leukocytes by this method.

Therefore attempts have been made in order to automatically classify and count a number of leukocytes to thereby increase accuracy and save labor. Recently, automated devices based on a flow system for solving the above-mentioned problems have been marketed.

These automated devices may be roughly classified into the following three types depending on the measurement principle.

A device of the first type consists of three lysing agents and three types of detection units. In the first step, cells other than leukocytes contained in a blood sample are lysed with the first lysing agent and RF and DC signals of the remaining leukocytes are measured. Then the leukocytes are classified into three types, namely lymphocytes, monocytes and granulocytes depending on the difference in the signal intensity.

The RF and DC signals will be now illustrated.

A direct current (DC) is applied between electrodes located at the both sides of a small aperture. Then a signal, which is produced due to a change in impedance upon the passage of a particle through the aperture, is referred to as a DC signal. On the other hand, a signal, which is produced due to a change in impedance upon the passage of a particle through the aperture when a radio-frequency (RF) current of several tens MHZ is applied between the electrodes, is referred to as an RF signal. Needless to say, both of these currents may be applied simultaneously and thus both of the DC and RF signals can be detected.

In the second step, cells other than eosinophils contained in the blood sample are lysed with the second lysing agent and the DC signals of the remaining cells are measured. Thus the eosinophils alone are classified and counted depending on the difference in the signal intensity.

In the third step, cells other than basophils contained in the blood sample are lysed with the third lysing agent and the DC signals of the remaining cells are measured. Thus basophils alone are classified and counted depending on the difference in the signal intensity.

Finally, the neutrophils are calculated by subtracting the eosinophils determined in the second step and the basophils determined in the third step from the granulocytes determined in the first step.

A device of the second type consists of one lysing agent and one detection unit. As Japanese Patent Laid-Open No. 502533/1989 describes in detail, this method comprises treating a blood sample with a lysing agent whereby blood corpuscles other than leukocytes can be lysed without damaging leukocytes, measuring RF, DC and scattered light signals at the same time and then classifying and counting five types of leukocytes by appropriately combining the above-mentioned three signals.

A device of the third type consists of two agents and two detection units. In this method, blood corpuscles other than leukocytes contained in a blood sample are first lysed with a lysing agent and then subjected to peroxidase-staining with a dye solution. Next, the absorbance and scattered light signal of each leukocyte are measured and the leukocytes are classified and counted into four types (lymphocytes, monocytes, neutrophils and eosinophils) depending on the difference in the signal intensity. Then the blood sample is treated with another lysing agent capable of lysing blood corpuscles other than basophils. After measuring two types of scattered light signals, the basophils are classified and counted depending on the difference in the signal intensity.

The above-mentioned disadvantages of the manual method are solved by each of these automated methods. From the viewpoint of precision, in particular, a remarkable improvement has been achieved. Thus these automated methods are almost satisfactory in the practice of clinical testing.

However none of these methods makes it possible to specifically classify and count immature granulocytes. Accordingly, there is a problem that a sample containing immature granulocytes cannot be accurately analyzed or the presence of immature granulocytes per se cannot be detected by these methods. In marketed devices, an abnormality in a scattergram due to the occurrence of immature granulocytes is detected and a warning of, for example, abnormal or suspect flag is given so as to urge re-examination with the manual method by a technician, thus minimizing overlooking of abnormalities. In this case, however, the re-examination with the manual method is required, which means the object of labor-saving is not completely achieved.

Separately, there have been reported some methods whereby fluorescence or scattered light of each leukocyte in a fluorochrome-stained blood sample are measured with a flow cytometer so as to classify leukocytes. Major examples of these methods are described in Japanese Patent Publication No. 853/1984, Japanese Patent Laid-Open No. 20820/1975 and Japanese Patent Publication No. 70166/1988.

Furthermore, we have proposed methods of classifying leukocytes with the use of the above-mentioned flow cytometer in Japanese Patent Laid-Open No. 134957/1988 entitled "METHOD OF CLASSIFYING LEUKOCYTES BY FLOW CYTOMETRY" and Japanese Patent Laid-Open No. 134958/1988 entitled "METHOD OF CLASSIFYING LEUKOCYTES BY FLOW CYTOMETRY AND REAGENTS USED IN THE METHOD.

When a specimen, obtained by eliminating influences of blood corpuscles other than leukocytes from a hematological sample by an appropriate method, is assayed with a marketed flow cytometer as shown in FIG. 1, it is generally known that a scattergram as shown in FIG. 2 is obtained and the leukocytes are divided into three subpopulations respectively comprising lymphocytes 1', monocytes 2' and granulocytes 3' mainly depending on the difference in the side scattered light intensity and each of these subpopulations can be easily classified and counted. It is also possible, further, to divide the granulocytes into subpopulations comprising eosinophils, basophils and neutrophils by combining the said process with the above-mentioned fluorochrome-staining.

In Japanese Patent Laid-Open No. 134958/1988, we have already disclosed a method of dividing leukocytes into five subpopulations and classifying and counting each subpopulation with the use of a flow cytometer and reagents to be used in this method. In this method, eosinophils and basophils are specifically fluorochrome-stained with Astrazon Yellow 3G. As the results of continuous studies, we have found out that Astrazon Yellow 3G further specifically stains immature granulocytes and thus allows the immature granulocytes to emit specific fluorescence to a degree comparable to eosinophils, as FIG. 3 shows. 1', 2', 3'', 4' and 5' respectively mean lymphocytes, monocytes, neutrophils, eosinophils and immature granulocytes, and basophils.

In this method, however, eosinophils are equivalent with immature granulocytes in intensity of fluorescence and fluorescent wavelength as well as in intensity of side scattered light signal. It is therefore impossible to separate eosinophils and immature granulocytes into different subpopulations.

In Japanese Patent Laid-Open No. 134957/1988, we have further disclosed a method for classifying leukocytes into five types with the use of a combination of Neutral Red, which specifically stains eosinophils, with Astrazon Orange G, which specifically stains basophils. In this method, it is also impossible to specifically stain immature granulocytes and, therefore, granulocytes cannot be separated from immature neutrophils.

On the other hand, U.S. Pat. No. 4,500,509 discloses a manual method for classifying and counting leukocytes wherein all leukocytes including immature granulocytes are fluorochrome-stained with Basic Orange 21 and then counted under a fluorescent microscope. However the above-mentioned disadvantages of the manual method cannot be solved by this method. Thus this U.S. patent provides no automated method.

SUMMARY OF THE INVENTION

As described above, the present invention aims at specifically detecting, classifying and counting immature granulocytes, which cannot be achieved by conventional automated methods, and providing a method for preparing a specimen for flow cytometry in order to classify and count immature granulocytes and to classify and count leukocytes involving immature granulocytes.

The above-mentioned objects of the present invention can be achieved by treating leukocytes with Astrazon Yellow 3G, capable of specifically staining basophils and immature granulocytes, and with Neutral Red, capable of specifically staining eosinophils and suppressing the specific staining of eosinophils with Astrazon Yellow 3G, at a pH value suitable for staining to thereby specifically fluorochrome-stain basophils, immature granulocytes and eosinophils.

Figure 1:
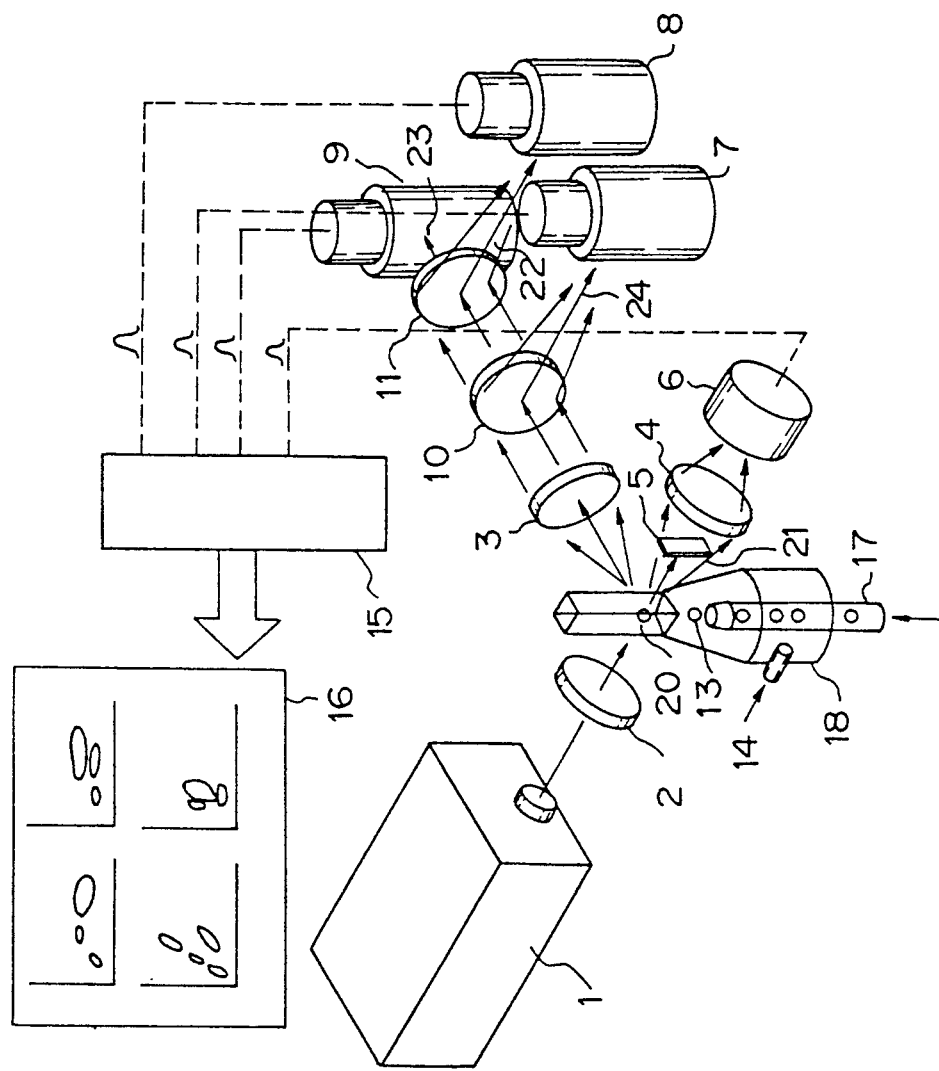
FIG. 1 is a schematic view showing the construction of a marketed flow cytometer to be used for embodying the present invention.

In these figures, each symbol has the following meaning.

1: light source,
2: lens,
3: condenser lens
4: condenser lens,
5: beam stopper,
6-9: light detection units,
10-11: dichroic mirror,
13: particle,
14: sheath fluid inlet,
15: signal-treatment unit,
16: analysis unit,
17: nozzle,
18: flow cell,
20: flow area of particle,
21: forward scattered light,
22: red fluorescence,
23: green fluorescence,
24: side scattered light,
1': lymphocytes,
2': monocytes,
3': granulocytes,
3'': neutrophils,
4': eosinophils, immature granulocytes,
5': basophils,
[R]: erythrocytes,
[Eo]: eosinophils,
[Granul]: granulocytes,
[Lym]: lymphocytes,
[Mono]: monocytes,
[Neut]: neutrophils,
[Ba]: basophils,
[Im]: immature granulocytes,
[Im1]: immature granulocyte group 1,
[Im2]: immature granulocyte group 2,
[A1]: subpopulation comprising leukocytes other than basophils, eosinophils and immatures,
[A2]: subpopulation comprising leukocytes other than eosionphils
[A3]: subpopulation comprising leukocytes other than basophils and immature granulocytes,
[A4]: subpopulation comprising leukocytes other than eosinophils, basophils and immature granulocytes,
[A5]: subpopulation comprising blood corpuscles other than eosinophils,
[A6]: subpopulation comprising lymphocytes and blood corpuscles other than leukocytes,
[A7]: subpopulation comprising blood corpuscles other than leukocytes,

[A8]: subpopulation comprising leukocytes alone,

[A9]: subpopulation comprising leukocytes other than eosinophils,

[A10]: subpopulation comprising blood corpuscles other than leukocytes,

[A11]: subpopulation comprising leukocytes other than eosinophils,

[A12]: subpopulation comprising blood corpuscles other than leukocytes,

[A13]: subpopulation comprising blood corpuscles other than eosinophils,

[A14]: subpopulation comprising blood corpuscles other than eosinophils,

[A15]: subpopulation comprising blood corpuscles other than basophils and immature granulocytes,

[A16]: population comprising blood corpuscles other than eosinophils,

[A17]: subpopulation comprising blood corpuscles other than monocytes, neutrophils, immature granulocytes 1, immature granulocytes 2 and basophils,

[A18]: population comprising leukocytes alone,

[A19]: population comprising leukocytes other than eosinophils,

[A20]: population comprising leukocytes other than eosinophils,

[A21]: population comprising leukocytes other than eosinophils,

[W1] to [W58]: windows 1 to 58.

DETAILED DESCRIPTION OF THE INVENTION

Now the present invention will be described in greater detail by citing a specimen, from which platelets and erythrocytes usually contained in a hematological sample have been eliminated by an appropriate method, by way of example.

Figure 4:
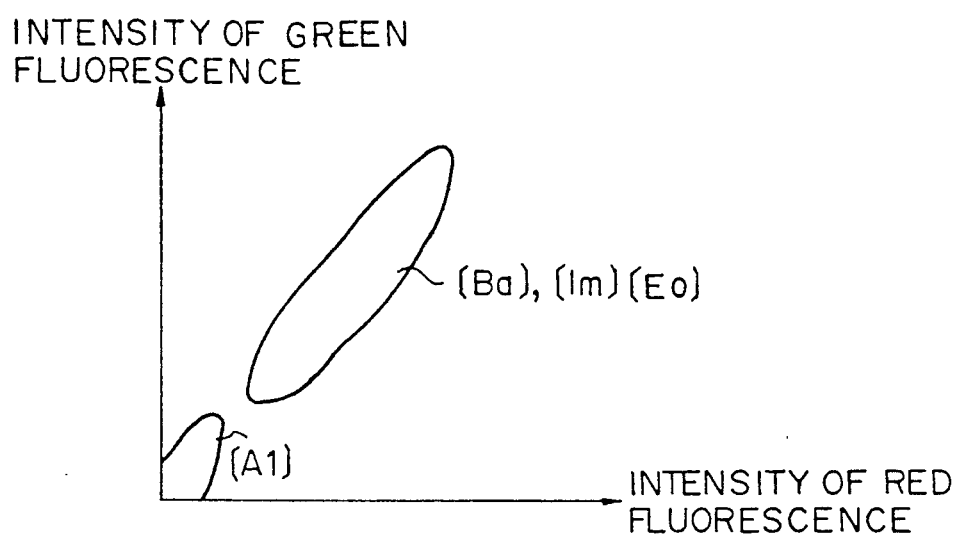
FIG. 4 is a scattergram wherein the intensity of green fluorescence and the intensity of red fluorescence due to staining with Astrazon Yellow 3G are referred to as the coordinate axes.
Figure 5:
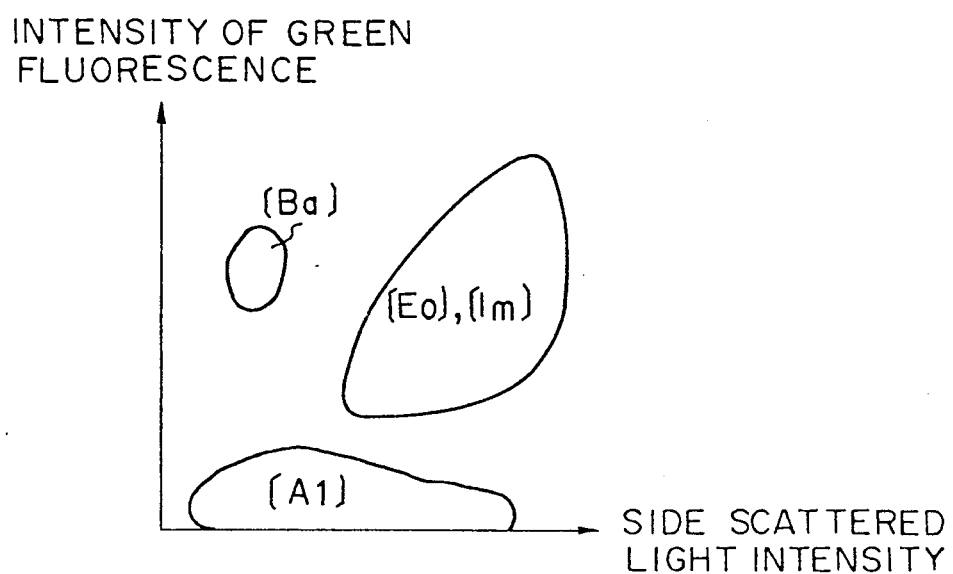
FIG. 5 is a scattergram wherein the side scattered light intensity and the intensity of green or red fluorescence obtained by staining a specimen with Astrazon Yellow 3G alone are referred to as the coordinate axes.

The characteristic principle of the present invention is based on the functions of two dyes. When the specimen is stained with Astrazon Yellow 3G alone, basophils, immature granulocytes and eosinophils are specifically fluorochrome-stained. After assaying with a flow cytometer, a scattergram is formed by referring the intensity of green fluorescence and that of red fluorescence to as the coordinate axes, as shown in FIG. 4. Thus leukocytes can be divided into two subpopulations depending on the difference in the intensity of green or red fluorescence, namely, one comprising basophils [Ba], immature granulocytes [Im] and eosinophils [Eo] and another one comprising other leukocytes [A1]. Alternately, another scattergram is formed by referring the side scattered light intensity and the intensity of green or red fluorescence to as the coordinate axes, as shown in FIG. 5. thus leukocytes can be divided into three subpopulations depending on the difference in the intensity of green or red fluorescence and the side scattered light intensity, namely, one comprising basophils [Ba], one comprising immature granulocytes [Im] and eosinophils [Eo] and one comprising other leukocytes [A1]. However it is impossible by this method to classify and count immature granulocytes alone.

Figure 6:
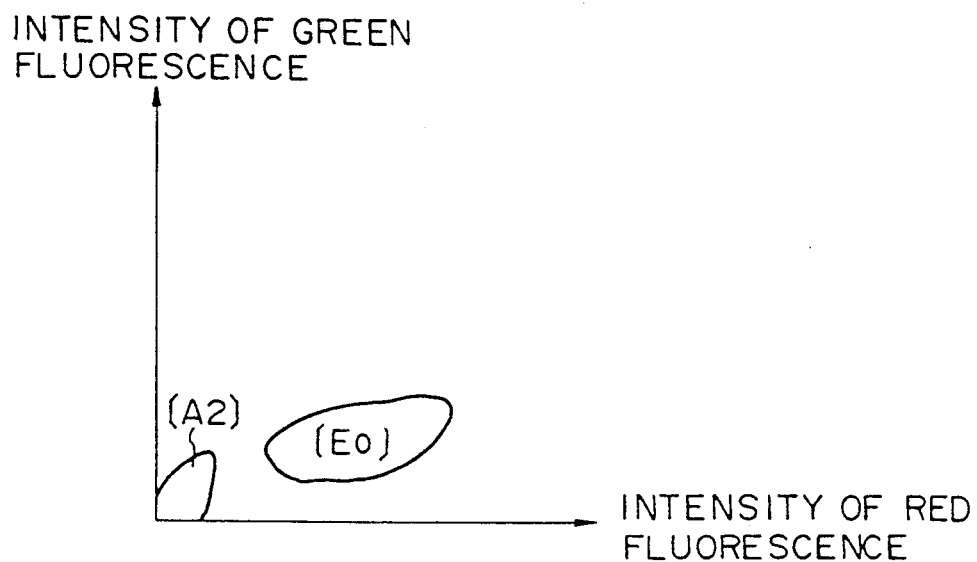
FIG. 6 is a scattergram wherein the intensity of red fluorescence and the intensity of green fluorescence obtained by staining a specimen with Neutral Red alone are referred to as the coordinate axes.
Figure 7:
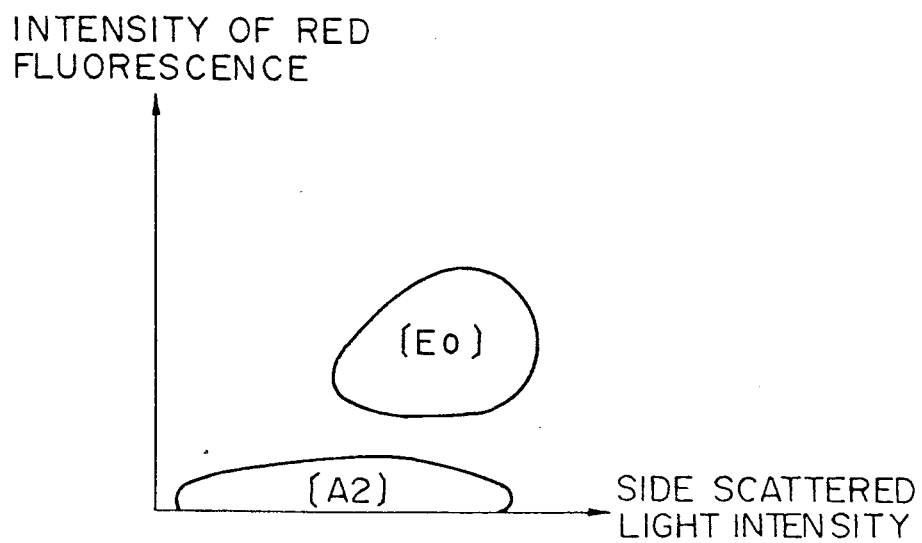
FIG. 7 is a scattergram wherein the side scattered light intensity and the intensity of red fluorescence obtained by staining a specimen with Neutral Red alone are referred to as the coordinate axes.

When the specimen is stained with Neutral Red alone, on the other hand, eosinophils are specifically fluorochrome-stained in red. After assaying with a flow cytometer, a scattergram is formed by referring the intensity of red fluorescence and that of green fluorescence to as the coordinate axes, as shown in FIG. 6. Alternately, another scattergram is formed by referring the side scattered light intensity and the intensity of red fluorescence to as the coordinate axes, as FIG. 7 shows. Thus leukocytes can be divided into two subpopulations depending on the difference in the intensity of red fluorescence, namely, one comprising eosinophils [Eo] and another one comprising other leukocytes other than eosinophils [A2]. However it is impossible to separate immature granulocytes alone by this method.

Figure 8:
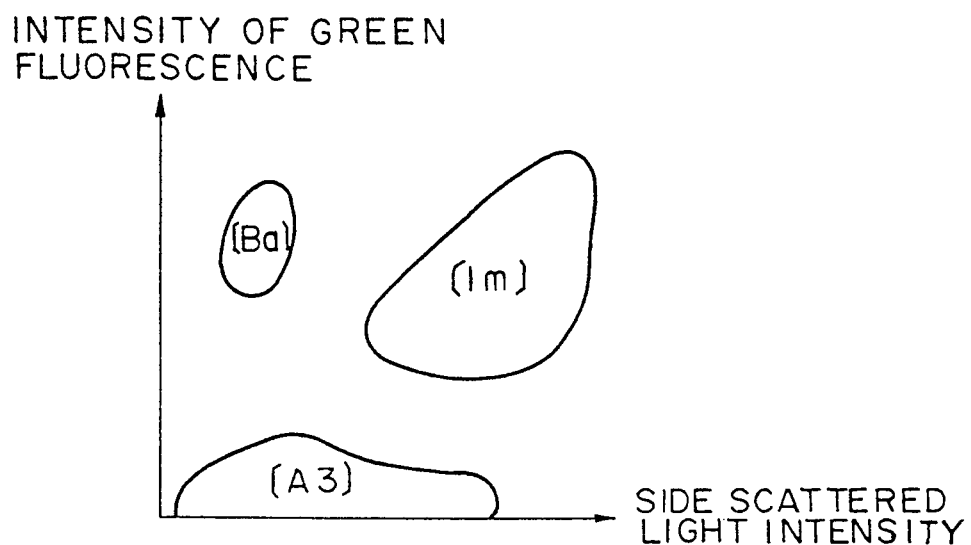
FIG. 8 is a scattergram wherein the intensity of green fluorescence and the side scattered light intensity obtained by staining a specimen in the coexistence of Astrazon Yellow 3G and Neutral Red are referred to as the coordinate axes.

When a specimen is fluorochrome-stained in the coexistence of Astrazon Yellow 3G and Neutral Red in accordance with the method of the present invention, Astrazon Yellow 3G specifically stains basophils and immature granulocytes. The staining of eosinophils with Astrazon Yellow 3G is suppressed by Neutral Red and thus no specific difference in the intensity of green fluorescence is observed. However eosinophils are specifically stained in red with Neutral Red. After assaying with a flow cytometer, a scattergram is formed by referring the intensity of green fluorescence and the side scattered light intensity to as the coordinate axes, as shown in FIG. 8. Thus leukocytes can be divided into three subpopulations, namely, one comprising basophils [Ba], one comprising immature granulocytes [Im] and one comprising other leukocytes [A3].

Figure 9:
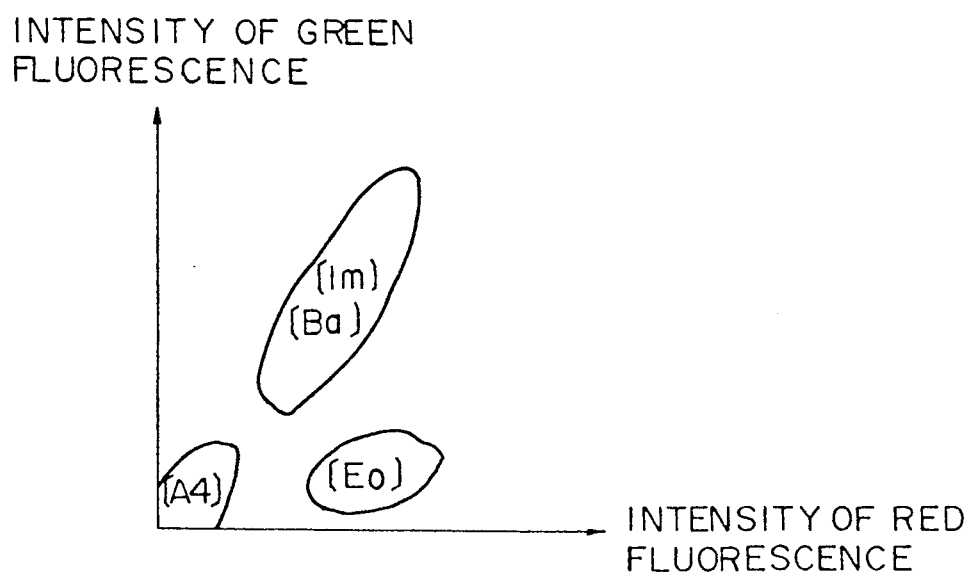
FIG. 9 is a scattergram wherein the intensity of red fluorescence and the intensity of green fluorescence obtained by staining a specimen in the coexistence of Astrazon Yellow 3G and Neutral Red are referred to as the coordinate axes.

When a scattergram is formed by referring the intensity of red fluorescence and that of green fluorescence to as the coordinate axes as shown in FIG. 9, the leukocytes can be divided into three subpopulations depending on the difference in the intensity of red or green fluorescence, namely, one comprising basophils [Ba] and immature granulocytes [Im], one comprising eosinophils [Eo] and one comprising other leukocytes [A4].

Although the staining mechanism of each dye has never been fully clarified, it is assumed that the staining would proceed as follows. It has been already known that each leukocyte contains substances specified below.

1. Basophils contain acidic mucopolysaccharides such as heparin in basophilic granules.

2. Immature granulocytes contain mucopolysaccharides in primary granules.

3. Eosinophils contain strongly basic substances characteristic to eosinophils in eosinophilic granules.

It is assumed that Astrazon Yellow 3G specifically stain the mucopolysaccharides described in the above 1. and 2. while Neutral Red specifically stains the strongly basic substances described in the above 3. and, therefore, a difference in the intensity of fluorescence, whereby blood corpuscles can be separated from each other, is observed when analyzed with a flow cytometer.

Figure 10:
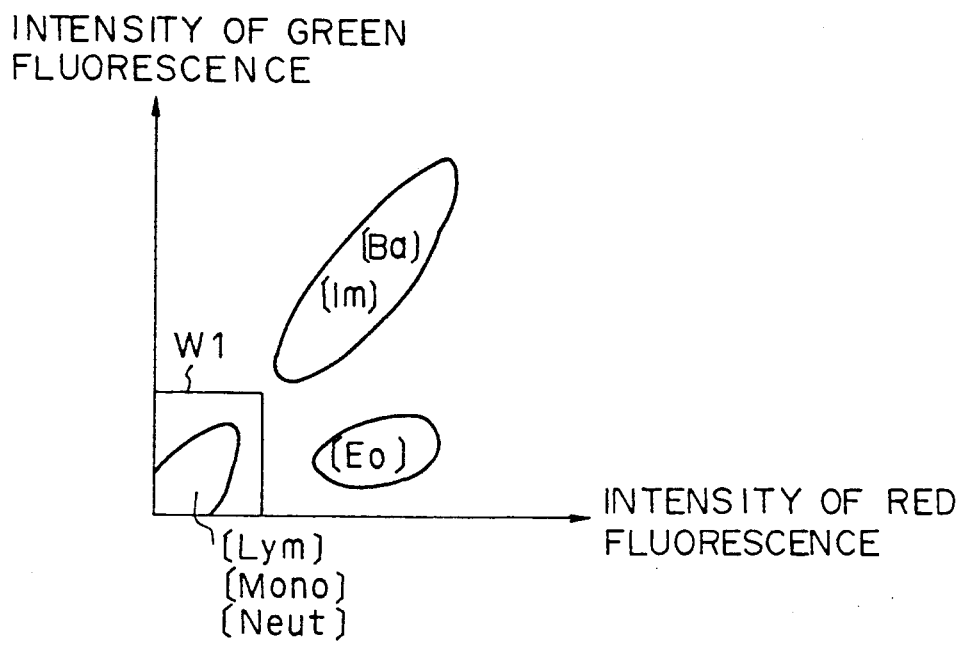
FIG. 10 is a scattergram wherein the intensity of red fluorescence and the intensity of green fluorescence obtained by staining a specimen with Astrazon Yellow 3G and Neutral Red are referred to as the coordinate axes.
Figure 11:
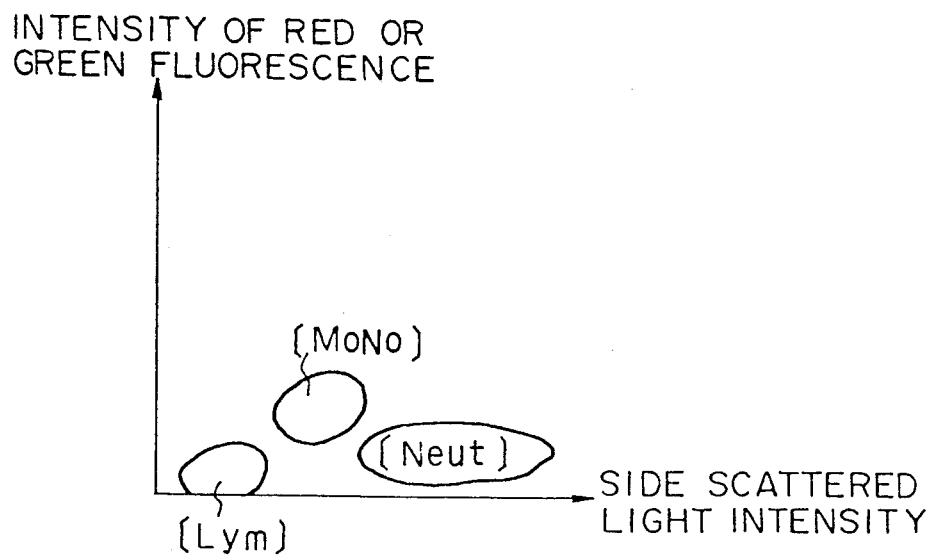
FIG. 11 is a scattergram wherein the side scattered light intensity and the intensity of green or red fluorescence of the data obtained from Window 1 [W1] of FIG. 10 are referred to as the coordinate axes.

As described above, immature granulocytes, basophils and eosinophils can be separated by means of specific fluorescence. However lymphocytes, monocytes and neutrophils contained in a blood sample scarcely contain the above-mentioned substances and, therefore, cannot be specifically stained. Although Astrazon Yellow 3G nonspecifically and weakly stains granules contained in lymphocytes, monocytes and neutrophils and thus these leukocytes emit slight fluorescence, these leukocytes can be hardly separated depending on the intensity of fluorescence. In order to classify these leukocytes, a scattergram is formed by referring the intensity of red fluorescence and that of green fluorescence to as the coordinate axes, as shown in FIG. 10. Then the data of a subpopulation comprising lymphocytes, monocytes and neutrophils [Lym+Mono+Neut] are taken out by a window 1 [W1] and another scattergram is formed by referring the side scattered light intensity and the intensity of red or green fluorescence as the coordinate axes, as shown in FIG. 11. Thus the lymphocytes [Lym], monocytes [Mono] and neutrophils [Neut] can be divided into three subpopulations, each comprising a single type of leukocytes, mainly depending on the difference in the side scattered light intensity.

A procedure for taking out a single subpopulation on a scattergram by enclosing within an area (i.e., a window), which is commonly employed in flow cytometry, is generally called "gating".

Further, leukocytes in each subpopulation can be counted by enclosing said subpopulation within a window and then counting blood corpuscles therein.

For example, the blood corpuscles can be counted by enclosing the subpopulation [Im] comprising blood corpuscles in FIG. 8 within a window and then counting the blood corpuscles. Similarly, each leukocyte subpopulation may be enclosed within a window followed by counting the blood corpuscles therein.

Hematological samples usually analyzed in clinical testing laboratories are peripheral blood which contains blood corpuscles other than leukocytes, mainly erythrocytes. When erythrocytes are contained in samples, the following influences are observed.

INFLUENCES OF ERYTHROCYTES

In general, a blood sample contains about 1,000 times in number as many as erythrocytes compared with leukocytes. However erythrocytes are never stained by the above-mentioned fluorochrome-staining method and thus emit little fluorescence. Thus erythrocytes exert no influence on the classification and counting of immature granulocytes, eosinophils and basophils each emitting specific fluorescence.

When leukocytes emitting no specific fluorescence (in particular, lymphocytes) are to be classified and counted, however, the presence of erythrocytes causes a problem. For example, lymphocytes cannot be completely separated from erythrocytes depending on the forward scattered light intensity or side scattered light intensity. In this case, therefore, it is impossible to accurately classify leukocytes.

Figure 2:
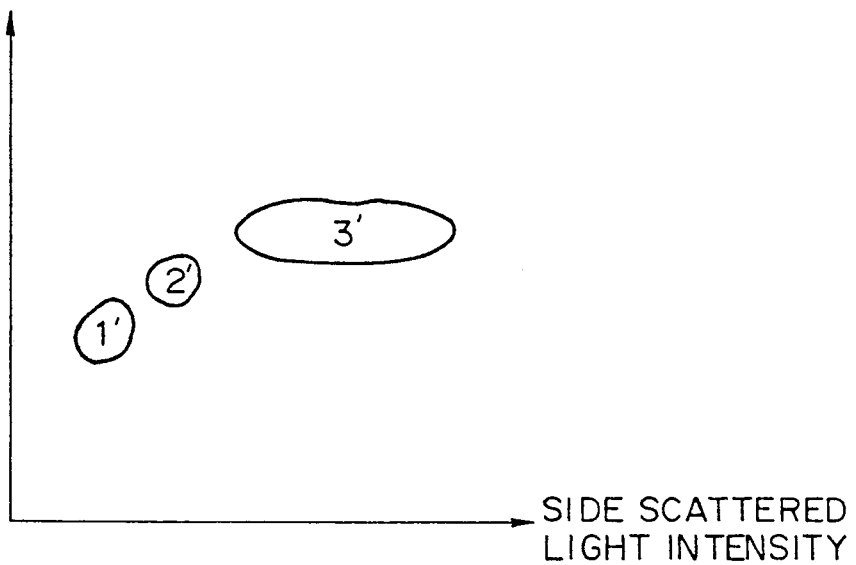
FIG. 2 is a scattergram obtained by measuring a specimen, which is prepared by eliminating influences of blood corpuscles other than leukocytes from a hematological sample, with the flow cytometer shown in FIG. 1.
Figure 3:
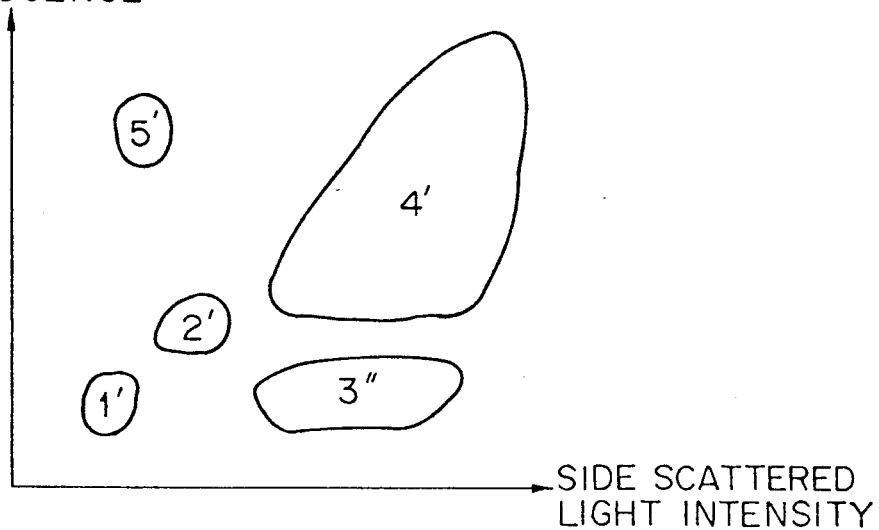
FIG. 3 is a scattergram wherein the intensity of fluorescence and side scattered light intensity due to staining with Astrazon Yellow 3G alone are referred to as the coordinate axes.
Figure 12:
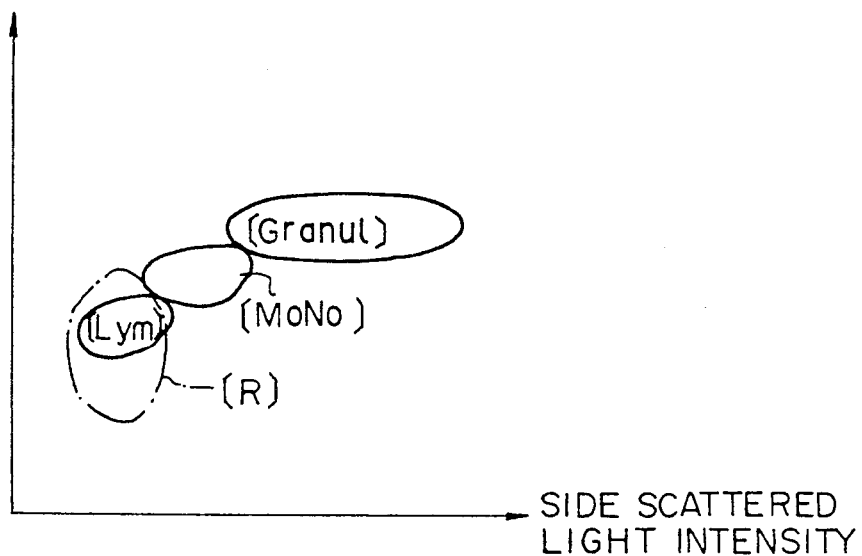
FIG. 12 is a scattergram wherein the side scattered light intensity and the forward scattered light intensity obtained when erythrocytes pass simultaneously are referred to as the coordinate axes.

When a large amount of erythrocytes pass through a detection unit of a flow cytometer simultaneously with leukocytes, furthermore, the intensity of scattered light signal of the leukocytes becomes inaccurate and, therefore, the classification of leukocytes [Lym], monocytes [Mono] and granulocytes [Granul], depending on scattered light, becomes difficult. FIG. 12 shows the distribution of scattered light intensity of leukocytes observed when erythrocytes pass simultaneously. The area [R] delineated with a single-dot chain line means the distribution of erythrocytes. As FIG. 12 shows, the intensity of forward scattered light and the intensity of side scattered light of erythrocytes are identical with lymphocytes and therefore lymphocytes cannot be separated from erythrocytes. Compared with FIG. 2 (a scattergram of a specimen from which the influences of erythrocytes have been eliminated), the distribution of the side scattered light intensity of each leukocyte is widened, which makes it difficult to separate the leukocyte subpopulations from each other. It is therefore required to eliminate the influences of erythrocytes from a blood sample in order to exactly classify leukocytes. Although there have been known several methods for removing erythrocytes from a blood sample, these conventional methods are disadvantageous in that, for example, a troublesome procedure is required or the staining of leukocytes is inhibited.

Problems in staining leukocytes are described in detail in Japanese Patent Laid-Open No. 134957/1988 and Japanese Patent Laid-Open No. 134958/1988. In these literature, furthermore, methods for eliminating the influences of erythrocytes for staining leukocytes are disclosed. These methods can be applied to the fluorochrome-staining in the method of the present invention, unexpectedly without essentially modifying.

Now these methods will be described in detail.

FIRST STEP FOR ELIMINATING INFLUENCES OF ERYTHROCYTES

In this step, erythrocytes alone are reduced into fragments in order to lower the scattered light intensity of the erythrocytes. Thus the influences on the scattered light of leukocytes due to the simultaneous passage of the erythrocytes and leukocytes can be eliminated and the erythrocyte fragments can be separated from leukocytes (in particular, lymphocytes).

In order to reduce erythrocytes into fragments without affecting the staining of leukocytes, a hematological sample is treated in the following manner. First, the hematological sample is treated under hypotonic and acidic conditions to thereby reduce erythrocytes into fragments. More particularly speaking, the erythrocytes are converted into ghosts and then reduced into fragments. When the erythrocytes are completely lysed, the pH value and osmotic pressure are controlled each to a level causing no damage on leukocytes. Thus erythrocytes can be reduced into fragments without damaging leukocytes.

As a result, the scattered light intensity of erythrocytes is reduced to a level corresponding to $\frac{1}{2}$ to $\frac{1}{3}$ of that of lymphocytes. Thus the simultaneous passage of erythrocytes with leukocytes is negligible in practice.

Figure 13:
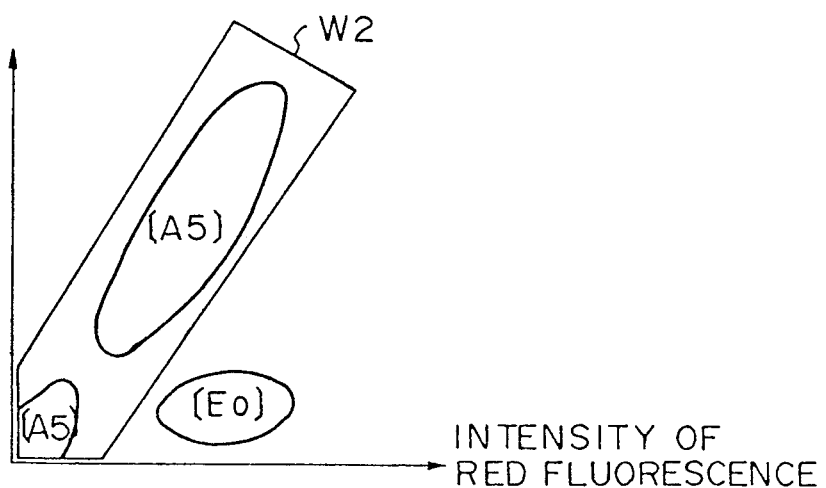
FIG. 13 is a scattergram wherein the intensity of red fluorescence and the intensity of green fluorescence are referred to as the coordinate axes.
Figure 14:
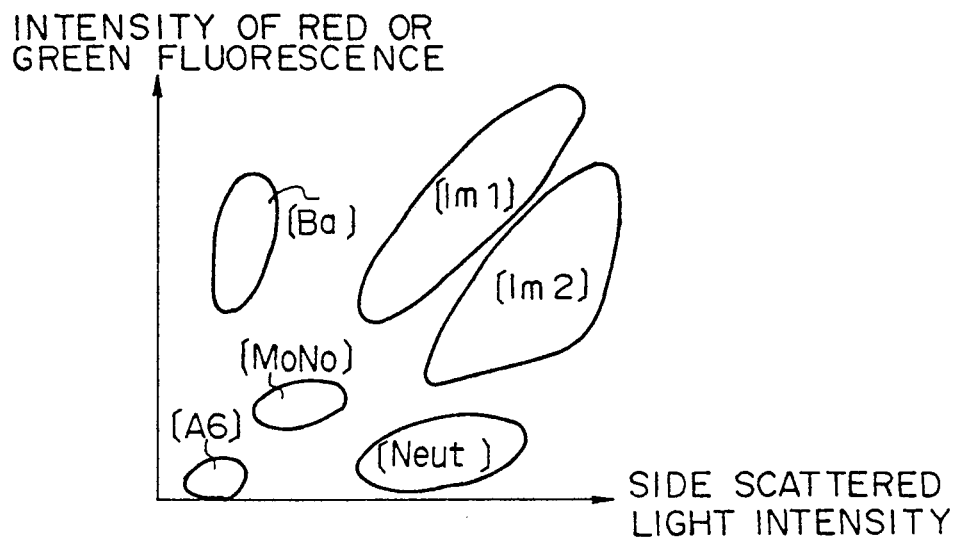
FIG. 14 is a scattergram wherein the intensity of red or green fluorescence of the data obtained from Window 2 [W2] of FIG. 13 is referred to as a coordinate axis.

When this method is applied to the above-mentioned staining method, the scattered light intensity of leukocytes can be measured at an extremely high accuracy. As FIG. 13 shows, for example, the data of a subpopulation [A5] comprising blood corpuscles other than eosinophils [Eo] are taken out by enclosing within a window 2 [W2] on a scattergram wherein the intensity of red fluorescence and the intensity of green fluorescence are referred to as the coordinate axes. As FIG. 14 shows, a scattergram wherein the intensity of green fluorescence and side scattered light intensity are referred to as the coordinate axes if formed. Then the subpopulation [A5] comprising blood corpuscles other than eosinophils is divided into six subpopulations, namely, one comprising basophils [Ba], one comprising neutrophils [Neut], one comprising monocytes [Mono], one comprising lymphocytes and erythrocyte fragments [A6] and, unexpectedly, two subpopulations of immature granulocytes [Im1] and [Im2]. Each of the leukocyte subpopulations is enclosed within a window and leukocytes therein are counted. Thus six leukocyte subpopulations can be classified and counted.

Figure 15:
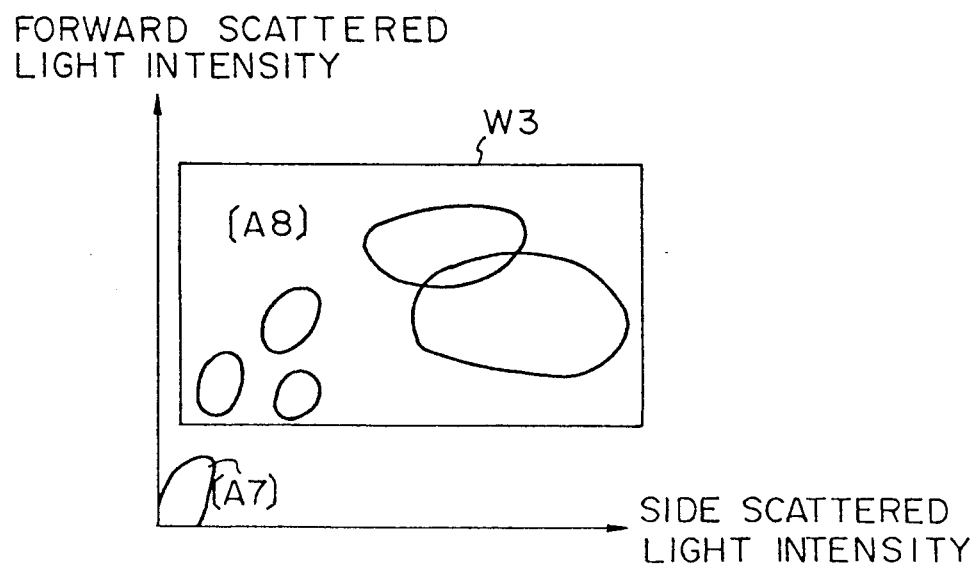
FIG. 15 is a scattergram wherein the forward scattered light intensity and the side scattered light intensity are referred to as the coordinate axes.
Figure 16:
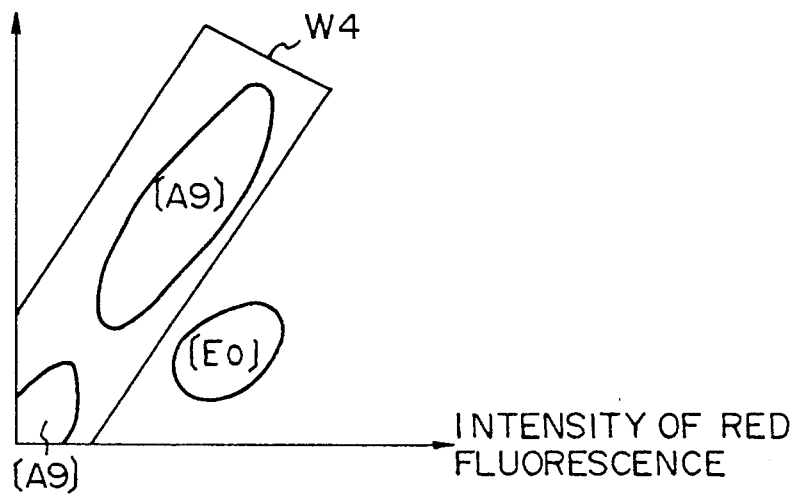
FIG. 16 is a scattergram wherein the intensity of red fluorescence and the intensity of green fluorescence of the data of the subpopulation [A8] in FIG. 15 are referred to as the coordinate axes.
Figure 17:
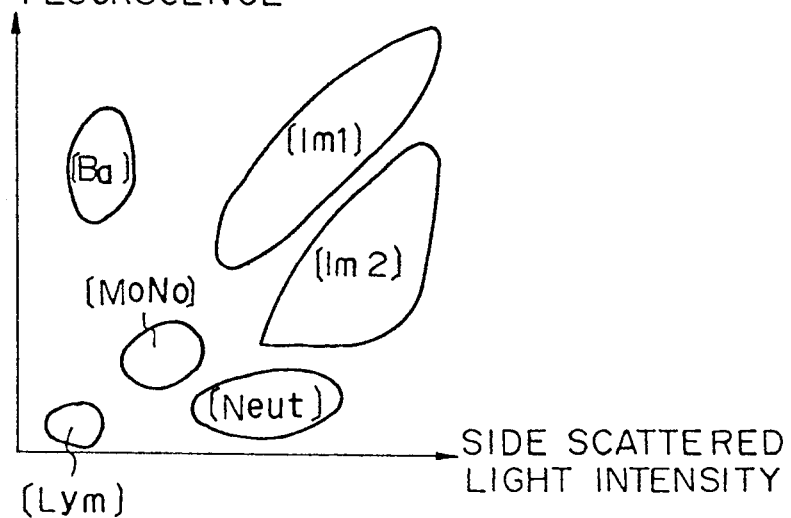
FIG. 17 is a scattergram wherein the side scattered light intensity and the intensity of red or green fluorescence of the data of the subpopulation [A9] in FIG. 16 are referred to as the coordinate axes.

On the other hand, as FIG. 15 shows, the subpopulation [A7] comprising erythrocyte fragments and platelets is eliminated and the data of the subpopulation [A8] comprising leukocytes alone are taken out, depending on the difference in the intensity of forward scattered light. Then a scattergram is formed by referring the intensity of red fluorescence and the intensity of green fluorescence to as the coordinate axes (FIG. 16). Thus the leukocytes are divided into eosinophils [Eo] and a subpopulation comprising leukocytes other than eosinophils [A9]. Further, the subpopulation [A9] is taken out with the window 4 [W4] and a scattergram is formed by referring the intensity of side scattered light and the intensity of red or green fluorescence to as the coordinate axes, as shown in FIG. 17. Thus the subpopulation [A9] is divided into six subpopulations, namely, one comprising lymphocytes [Lym], one comprising monocytes [Mono], one comprising neutrophils [Neut], one comprising basophils [Ba], one comprising immature granulocytes 1 [Im1] and another one comprising immature granulocytes 2 [Im2]. In this case, therefore, seven leukocyte subpopulations can be classified and counted.

SECOND STEP FOR ELIMINATING INFLUENCES OF ERYTHROCYTES

In order to separate leukocytes (in particular, lymphocytes), which are not stained with the above-mentioned Astrazon Yellow 3G or Neutral Red, from erythrocytes, leukocytes are treated with a third dye capable of nonspecifically staining leukocytes so as to exclusively stain leukocytes. Then erythrocytes are separated from leukocytes depending on the difference in the intensity of fluorescence.

A fluorescent dye to be used here is selected from among those which never inhibit the specific staining with Astrazon Yellow 3G and Neutral Red and can stain substances contained exclusively in leukocytes. Components existing in leukocytes alone involve nuclei and cytoplasm, since eosinophils have neither nuclei nor cytoplasm.

Accordingly, a dye capable of staining either nuclei or cytoplasm or both of these substances should be selected here. Examples of a dye satisfying this requirement are as follows.

(1) Astrazon Orange R (CI No. 48,040, CU Basic Orange 22)
(2) Astra Violet (CI No. 48070, Basic Red 12)
(3) Rhodamine 6G (CI No. 45160)
(4) Rhodamine 19
(5) Rhodamine B (CI No. 45170, Basic Violet 10)
(6) Rhodamine 3GO (CI No. 45210, Basic Red 3)
(7) Pyronine B (CI No. 45010)
(8) Cyanosine
(9) 3,3'-dimethylthiocarbocyanine iodide
(10) 3,3'-diethylthiocarbocyanine iodide
(11) 3,3'-dipropyloxacarbocyanine iodide
(12) 3,3'-dihexyloxacarbocyanine iodide
(13) 3,6-bis(dimethylamino)-10-dodecylacridinium bromide
(14) 7-benzylamino-4-nitrobenzoxadiazole
(15) 7-fluoro-4-nitrobenzoxadiazole
(16) Astrazon Red 6B (CI No. 48020, Basic Violet 7).

Although the effects of these dyes have been confirmed by us, the present invention is not restricted thereto. Namely, any dye may be used so long as it satisfies the above-mentioned requirements.

When this method is combined with the above-mentioned staining method, leukocytes can be finally classified into at least six subpopulations respectively comprising eosinophils, immature granulocytes, basophils, neutrophils, monocytes and lymphocytes and the blood corpuscles contained in each subpopulation can be counted. When a scattergram is formed by referring the intensity of red fluorescence and the intensity of green fluorescence to as the coordinate axes (FIG. 18), for example, a subpopulation comprising blood corpuscles other than leukocytes [A10], a subpopulation comprising eosinophils [Eo], a subpopulation comprising leukocytes other than eosinophils [A11] are observed and, therefore, the eosinophils can be classified and counted.

Figure 19:
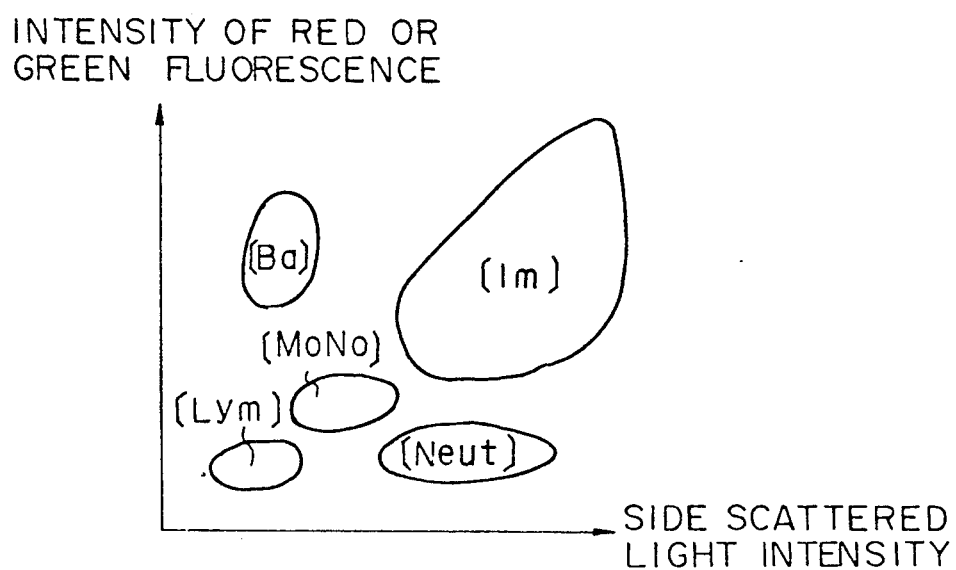
FIG. 19 is a scattergram wherein the side scattered light intensity and the intensity of red or green fluorescence of the data of the subpopulation [A11] in FIG. 18 are referred to as the coordinate axes.

Then the data of the subpopulation [A11] comprising leukocytes other than eosinophils are taken out with a window 5 [W5] and a scattergram is formed by referring the side scattered light intensity and the intensity of red or green fluorescence to as the coordinate axes, as shown in FIG. 19. Thus the leukocyte subpopulation [A11] is divided into five subpopulations, namely, one comprising lymphocytes [Lym], one comprising monocytes [Mono], one comprising neutrophils [Neut], one comprising basophils [Baso] and one comprising immature granulocytes [Im] and leukocytes in each subpopulation can be classified and counted.

In this method, however, the phenomenon that the simultaneous passage of erythrocytes and leukocytes makes the scattered light intensity of leukocytes somewhat inaccurate cannot be denied. Thus it is difficult to separate immature granulocytes into two groups.

Third Method for Eliminating Influences of Erythrocytes

Figure 20:
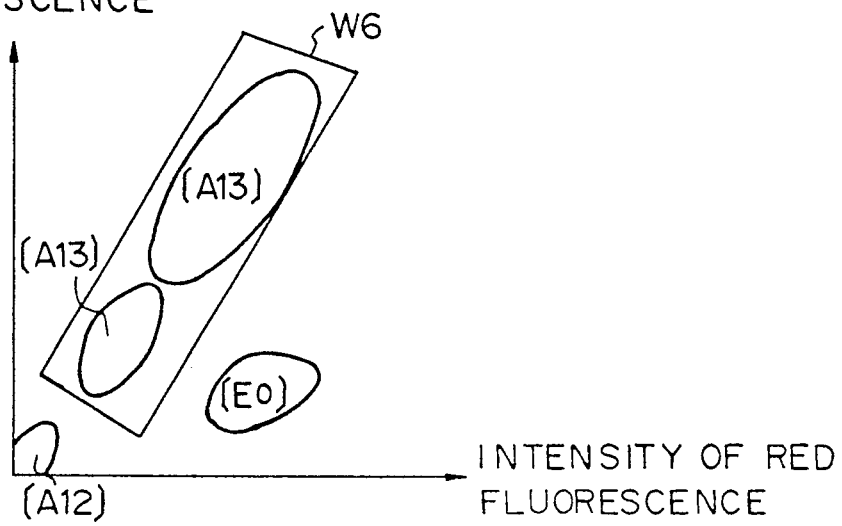
FIG. 20 is a scattergram wherein the intensity of red fluorescence and the intensity of green fluorescence are referred to as the coordinate axes.

The two steps for eliminating influences of erythrocytes as described above can be applied, either separately or simultaneously, to the above-mentioned method for staining leukocytes without essentially modifying. Thus all leukocytes including lymphocytes can be separated from other blood corpuscles depending on the difference in the intensity of fluorescence and the side scattered light of leukocytes can be accurately measured. When a scattergram is formed by referring the intensity of red fluorescence and the intensity of green fluorescence to as the coordinate axes, as shown in FIG. 20, three subpopulations, namely, one comprising blood corpuscles other than leukocytes [A12], one comprising eosinophils [Eo] and one comprising leukocytes other than eosinophils [A13] are observed. Thus the eosinophils can be classified and counted.

Figure 21:
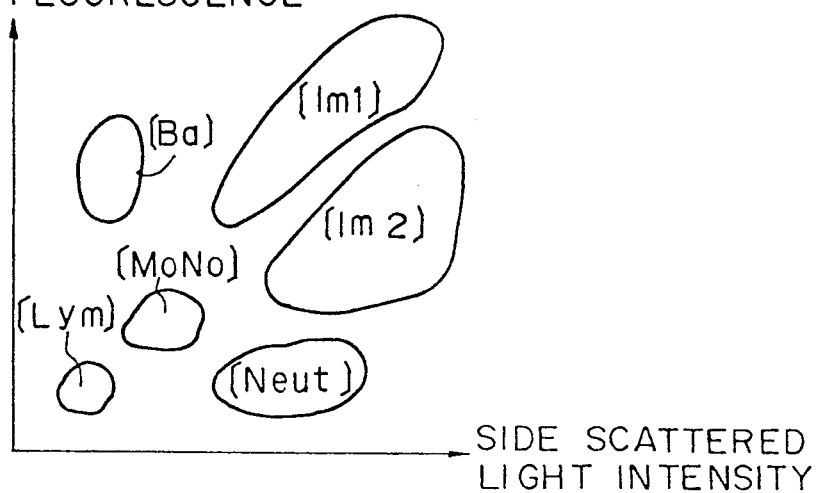
FIG. 21 is a scattergram wherein the side scattered light intensity and the intensity of red or green fluorescence of the data of the subpopulation [A13] in FIG. 20 are referred to as the coordinate axes.

Then the data of the subpopulation [A13] are taken out by enclosing within a window 6 [W6] and a scattergram is formed by referring the side scattered light intensity and the intensity of red or green fluorescence to as the coordinate axes (refer to FIG. 21). Thus six subpopulations including one comprising lymphocytes [Lym], one comprising monocytes [Mono], one comprising neutrophils [Neut], one comprising basophils [Baso], one comprising immature granulocytes 1 [Im1] and another one comprising immature granulocytes 2 [Im2] are formed and the leukocytes in each subpopulation can be classified and counted.

Now structures of the dye to be used in the method of the present invention will be given.

Astrazon Yellow 3G (CI No. 48.055, CI Basic Yellow 11)

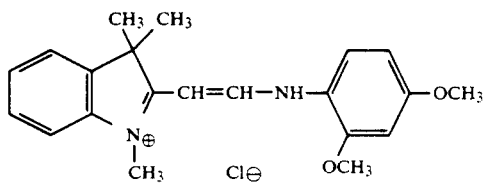

Neutral Red (CI No. 50,040, CI Basic Red 5)

-continued

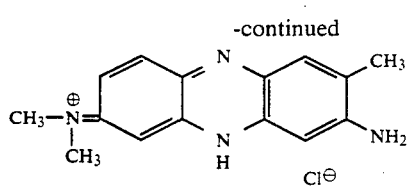

Astrazon Orange R (CI No. 48,040, CI Basic Orange 22)

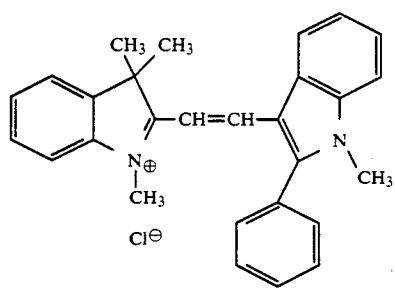

Astrazon Violet (CI No. 48,070, Basic Red 12)

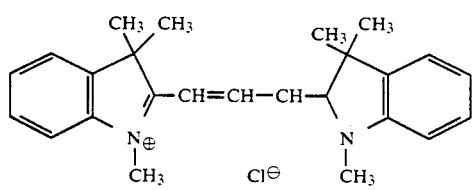

Rhodamine 6G (CI No. 45,160)

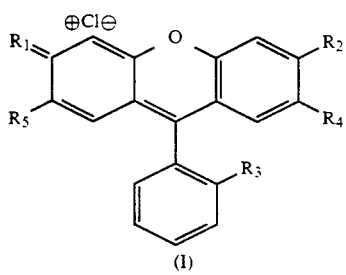

(I)

In formula (I), $R_1$: $=N^+HC_2H_5$,
$R_2$: $-NH-C_2H_5$
$R_3$: $-COOC_2H_5$,
$R_4$, $R_5$: $-CH_3$.

Rhodamine 19

In formula (I), $R_1$: $=N^+H-C_2H_5$
$R_2$: $-NH-C_2H_5$
$R_3$: $-COOH$,
$R_4$, $R_5$: $-CH_3$.

Rhodamine B (CI No. 45,170, Basic Violet 10)

In formula (I), $R_1$: $=N^+H_2$.
$R_2$: $-NH_2$.
$R_3$: $-COOCH_3$,
$R_4$, $R_5$: $-H$.

Rhodamine 3GO (CI No. 45,210, Basic Red 3)

In formula (I), $R_1$: $=N^+H-CH_3$,
$R_2$: $-NH_2$.
$R_3$: $-COOCH_3$,
$R_4$: $-CH_3$.
$R_5$: $-H$.

Pyronine B (CI No. 45,010)

-continued

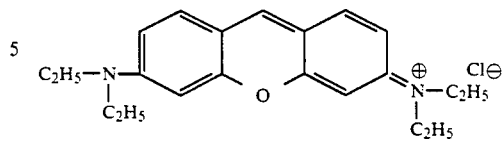

Cyanosine

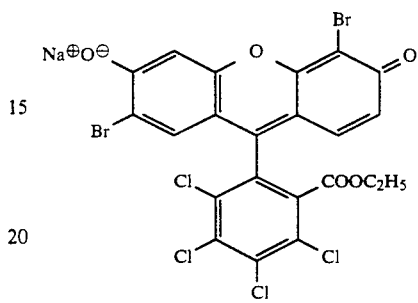

3,3'-Dimethylthiocarbocyanine iodide

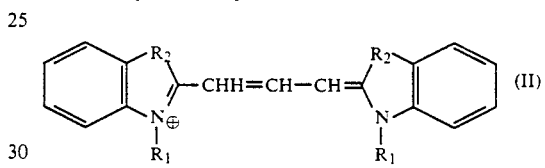

In formula (II). $R_1$: $-CH_3$.
$R_2$: $-S-$.

3,3'—Diethylthiocarbocyanine iodide

In formula (II). $R^1$: $-C_2H_5$.
$R_2$: $-S-$.

3,3'—Dipropyloxacarbocyanine iodide

In formula (II). $R_1$: $-C_3H_7$.
$R_2$: $-O-$.

3,3'—Dihexyloxacarbocyanine iodide

In formula (II). $R^1$: $-C_6H_{13}$.
$R_2$: $-O-$.

3,6'—Bis(dimethylamino)-10-dodecylacridinium bromide

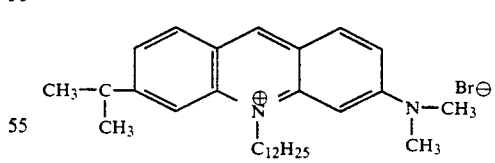

7-Benzylamino-4-nitrobenzoxadiazole

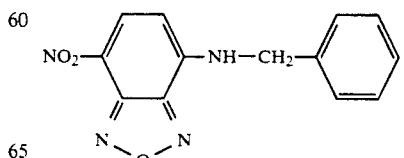

7-Fluoro-4-nitrobenzoxadiazole

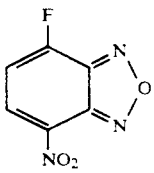

Astrazon Red 6B (CI No. 48,020, Basic Violet 7).

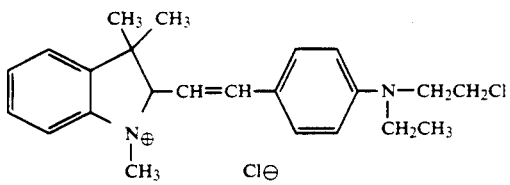

The term "hematological sample" as used herein means a biological sample mainly comprising blood cells which is obtained from animal (in particular, human) peripheral blood or bone marrow punctate. A preferable example thereof is venous blood which has been treated with an anticoagulant. Further, a specimen obtained by previously eliminating blood corpuscles other than leukocytes from the above-mentioned hematological sample by a suitable method such as density gradient centrifugation may be preferably used in the present invention.

The terms "basophils" and "eosinophils" as used herein respectively mean basophils and eosinophils identified by the manual method by means of Romanovsky's stain. Immature granulocytes consist of promyelocytes, myelocytes and metamyelocytes identified by the manual method. The above-mentioned two groups of immature granulocytes involve the immature granulocyte group 1 mainly comprising promyelocytes, in which the presence of primary granules (azure granules) is identified, and another group 2 mainly comprising myelocytes and metamyelocytes, in which little primary granules are identified.

A flow cytometer is a device by which at least three optical data (red fluorescence, green fluorescence, side scattered light), preferably four optical data (forward scattered light and the above-mentioned three factors) can be measured, as shown in FIG. 1. Thus types of cells can be analyzed depending on these four optical data. In the present invention, a commonly marketed flow cytometer or those comparable thereto in function may be employed. Detailed description on flow cytometer will be given later.

In a preferred embodiment of the present invention, a hematological sample is mixed with an aqueous solution comprising Astrazon Yellow 3G in an amount sufficient at least for specifically staining basophils and immature granulocytes, Neutral Red in an amount sufficient for specifically staining eosinophils and a buffer for adjusting the pH value to a level suitable for specifically staining the basophils, immature granulocytes and eosinophils in said hematological sample to thereby specifically fluorochrome-stain at least the basophils, immature granulocytes and eosinophils. The amount of Astrazon Yellow 3G sufficient at least for specifically staining basophil and immature granulocyte corresponds to a concentration of 50 mg/l or above in the aqueous solution. It has been confirmed that the upper limit of the concentration of Astrazon Yellow 3G for achieving the effects of the present invention is 1,000 mg/l. However this does not mean that the effects of the present invention would disappear at a concentration exceeding the above-mentioned level.

The amount of Neutral Red sufficient for specifically staining eosinophils corresponds to a concentration of 1 mg/l or above in the aqueous solution. Still preferably, the concentration of Neutral Red ranges from 1/50 to 1/10 of the Astrazon Yellow 3G concentration. The staining with Astrazon Yellow 3G is competitive with the staining with Neutral Red and, therefore, an extremely high concentration of Neutral Red, compared with the Astrazon Yellow 3G concentration, would inhibit not only the staining of eosinophils with Astrazon Yellow 3G but also the specific staining of basophils and immature granulocytes.

The pH value of the mixture of said aqueous solution with the hematological sample suitable for specifically staining basophils, immature granulocytes and eosinophils ranges from 7.0 to 11.0, still preferably from 7.5 to 10.0. When the pH value of the mixture is lower than 7.0, basophils and immature granulocytes can be hardly stained with Astrazon Yellow 3G effectively. When the pH value exceeds 11.0, on the other hand, leukocytes are seriously damaged and often changed in shape. In this case, furthermore, the decomposition of Astrazon Yellow 3G causes the formation of precipitates which interfere the measurement with a flow cytometer.

The most appropriate procedure for maintaining the pH value of the mixture at a level suitable for staining comprises using a buffer. Any buffer may be arbitrarily used in the present invention without restriction, so long as its pKa (acid dissociation constant) is around 9.0±2.0. The concentration of the buffer may preferably range from 5 to 100 mM/l, though it is not particularly restricted. In the embodiment of the method of the present invention, it is not essentially required to use a buffer. Namely, any other method may be employed so as to adjust the pH value from 7.0 to 11.0.

The mixing ratio by volume of the hematological sample to the aqueous solution is not particularly restricted. In the measurement with a flow cytometer, the mixing ratio may preferably range from 1:5 to 1:200.

The time required for completing the staining somewhat depends on temperature. At a room temperature (18° to 25° C.), the staining may be completed within 10 to 40 seconds. The staining period is somewhat shortened at a higher temperature and, on the contrary, somewhat prolonged at a lower temperature.

In order to prevent leukocytes from being damaged and to maintain at least lymphocytes, monocytes and neutrophils in a shape required for separation depending on scattered light, the osmotic pressure may preferably range from 100 to 500 mOsm/kg, still preferably from 200 to 400 mOsm/kg.

When the osmotic pressure of the mixture does not fall within the range as specified above, it is recommended to add an osmolarity compensating agent to the aqueous solution. As the osmolarity compensating agent, those commonly employed for maintaining biological cells at physiological osmotic pressure (for example, alkali metal salts and saccharides) may be preferably used, though the present invention is not restricted thereto.

When the specimen thus obtained is assayed with a flow cytometer, leukocytes can be divided into at least three subpopulations respectively comprising basophils [Ba], immature granulocytes [Im] and eosinophils [Eo], as FIGS. 8 and 9 show. Thus each subpopulation can be classified and counted.

Now, a method for preparing a specimen wherein a step for eliminating the influences of erythrocytes involves a first step for lysing erythrocytes will be described.

First, a hematological sample is mixed with a first aqueous solution of an acidic pH and hypotonic and thus erythrocytes are converted into ghosts and then reduced into fragments.

After the completion of the lysing of erythrocytes, a second aqueous solution, which contains a buffer for neutralizing the acid and an osmolarity compensating agent for controlling the osmotic pressure at a level for maintaining the shape of leukocytes, is added to the mixture before leukocytes undergo morphological changes. Thus a hematological sample, from which the influences of erythrocytes have been eliminated, is obtained.

The above step for reducing erythrocytes alone into fragments with the use of an acidic subtonic solution is described in greater detail in Japanese Patent Laid-Open No. 134957/1988.

The hematological sample, from which the influences of erythrocytes have been eliminated as described above, is then fluorochrome-stained with Astrazon Yellow 3G and Neutral Red. Thus a specimen for the measurement with a flow cytometer is obtained.

The term "acidic" as used above preferably means a pH value of from 2.0 to 5.0, still preferably from 2.5 to 4.0.

The buffer to be used in the first step is not particularly restricted and those having pKa of 3.0±2.0 may be preferably employed therefor.

The buffer is used at a concentration required for maintaining the pH value of the mixture from 2.0 to 5.0. It is preferable that the buffer concentration ranges from 5 to 50 mM/l.

When the pH value is lower than 2.0, the specific stain of leukocytes is evidently inhibited. When the pH value exceeds 5.0, on the other hand, the reduction of erythrocytes into fragments is evidently inhibited.

The term "hypotonic" as used above means an osmotic pressure of 100 mOsm/kg or below. When the osmotic pressure exceeds 100 mOsm/kg, the reduction of erythrocytes into fragments is evidently inhibited.

The reaction time of the first aqueous solution with the hematological sample required for reducing erythrocytes into fragments somewhat depends on temperature. At room temperature (18° to 25° C.), it is completed within 5 to 20 seconds.

The reaction time is somewhat shortened at a higher temperature and, on the contrary, somewhat prolonged at a lower temperature.

The step for specifically fluorochrome-staining basophils, immature granulocytes and eosinophils can be performed simultaneously with the step for reducing erythrocytes into fragments.

For example, this can be achieved as follows. First, a hypotonic (and acidic) first aqueous solution comprising Astrazon Yellow 3G and Neutral Red for specifically staining leukocytes and a buffer for maintaining the mixture acidic is mixed with a hematological sample and thus erythrocytes are reduced into fragments. Then a second aqueous solution comprising a buffer for neutralizing said acid in the buffer in the first fluid and maintaining a pH suitable for staining and an osmolarity compensating agent for controlling the osmotic pressure at a level required for maintaining the shape of leukocytes is further added.

When the specimen prepared by this method is assayed with a flow cytometer, leukocytes can be divided into six subpopulations, namely, one comprising eosinophils [Eo], one comprising monocytes [Mono], one comprising neutrophils [Neut], one comprising basophils [Ba], one comprising immature granulocytes 1 [Im1] and another one comprising immature granulocytes 2 [Im2], as FIGS. 13 and 14 show. Thus each leukocytes can be classified and counted.

In the above example, the optical informations to be measured include three factors, i.e., green fluorescence, red fluorescence and side scattered light. When four optical factors (forward scattered light is added to the above-mentioned three ones) are measured, leukocytes can be divided into seven subpopulations, namely, one comprising eosinophils [Eo], one comprising lymphocytes [Lym], one comprising monocytes [Mono], one comprising neutrophils [Neut], one comprising basophils [Ba], one comprising immature granulocytes 1 [Im1] and another one comprising immature granulocytes 2 [Im2] as FIGS. 15, 16 and 17 show. Thus each leukocytes can be classified and counted.

Now, a method for preparing a specimen wherein a step for eliminating the influences of erythrocytes involves a second step for staining exclusively leukocytes will be described.

In this second step, a dye capable of staining leukocytes (in particular, lymphocytes) which are not fluorochrome-stained with Astrazon Yellow 3G or Neutral Red, without inhibiting the staining with Astrazon Yellow 3G and Neutral Red is used. Thus a specimen for separating leukocytes from erythrocytes depending on the difference in the intensity of fluorescence at the measurement with a flow cytometer is obtained.

The dye to be used in this step may be selected from among those capable of staining substances contained in leukocytes alone without staining erythrocytes. For this purpose, a dye capable of staining either nuclei or cytoplasm or both of them is to be used.

Particular examples of dyes usable for this purpose are as follows.

(1) Astrazon Orange R (CI No. 48040, CI Basic Orange 22)
(2) Astra Violet (CI No. 48070, Basic Red 12)
(3) Rhodamine 6G (CI No. 45160)
(4) Rhodamine 19
(5) Rhodamine B (CI No. 45170, Basic Violet 10)
(6) Rhodamine 3GO (CI No. 45210, Basic Red 3)
(7) Pyronine B (CI No. 45010)
(8) Cyanosine
(9) 3,3'-dimethylthiocarbocyanine iodide
(10) 3,3'-diethylthiocarbocyanine iodide
(11) 3,3'-dipropyloxacarbocyanine iodide
(12) 3,3'-dihexyloxacarbocyanine iodide
(13) 3,6-bis(dimethylamino)-10-dodecylacridinium bromide
(14) 7-benzylamino-4-nitrobenzoxadiazole
(15) 7-fluoro-4-nitrobenzoxadiazole
(16) Astrazon Red 6B (CI No. 48020, Basic Violet 7).

In a preferable embodiment of the present invention, a hematological sample is mixed with an aqueous solution comprising Astrazon Yellow 3G capable of specifically staining basophils and immature granulocytes, Neutral Red, capable of specifically staining eosinophils, a buffer for adjusting the pH value of the mixture at a level suitable for staining and at least one dye selected from among those cited above. This aqueous solution may further contain an osmolarity compensating agent.

The optimum concentration of the dye capable of staining at least one of nuclei and cytoplasm of leukocytes vary from dye to dye. Therefore the optimum concentration is to be experimentally determined.

Figure 18:
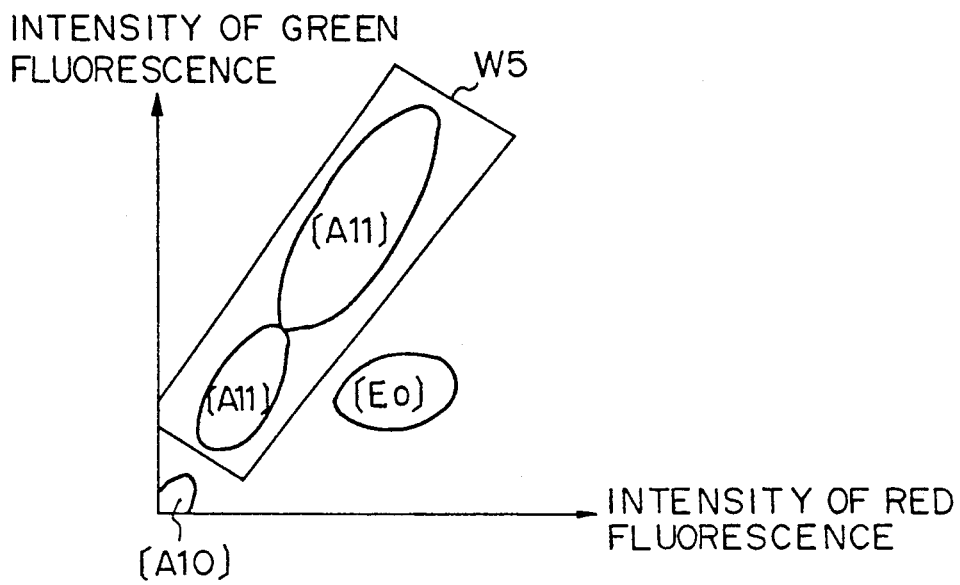
FIG. 18 is a scattergram wherein the intensity of red fluorescence and the intensity of green fluorescence are referred to as the coordinate axes.

When the specimen prepared by this method is assayed with a flow cytometer, leukocytes can be divided into six subpopulations respectively comprising eosinophils [Eo], lymphocytes [Lym], monocytes [Mono], neutrophils [Neut], basophils [Ba] and immature granulocytes [Im], as FIGS. 18 and 19 show. Thus each leukocytes can be classified and counted.

This second step for staining the nuclei or cytoplasm of leukocytes can be performed simultaneously with the first step for reducing erythrocytes into fragments.

For example, this can be achieved as follows. First, an acidic and hypotonic first aqueous solution comprising Astrazon Yellow 3G and Neutral Red for specifically staining leukocytes and at least one dye selected from these listed above and a buffer for maintaining the mixture acidic is mixed with a hematological sample and thus erythrocytes are reduced into fragments. Then a second aqueous solution comprising a buffer for neutralizing said acid in the buffer in the first solution and maintaining a pH suitable for staining and an osmolarity compensating agent for controlling the osmotic pressure at a level required for maintaining the shape of leukocytes is further added.

When the specimen prepared by this method is assayed with a flow cytometer, leukocytes can be divided into seven subpopulations, namely, one comprising eosinophils [Eo], one comprising lymphocytes [Lym], one comprising monocytes [Mono], one comprising neutrophils [Neut], one comprising basophils [Ba], one comprising immature granulocytes 1 [Im1] and another one comprising immature granulocytes 2 [Im2] simply by measuring three optical signals (i.e., red fluorescence, green fluorescence, side scattered light), as FIGS. 20 and 21 show. Thus each leukocytes can be classified and counted.

EXAMPLES

To further illustrate a preferable embodiment of the present invention, and not by way of limitation, the following Examples will be given.

Now, a flow cytometer to be used in the embodiment of the present invention will be illustrated. FIG. 1 is a schematic diagram showing the construction of a common flow cytometer. In FIG. 1, 1 is a light source of the flow cytometer from which light of a wavelength suitable for exciting the specific fluorescence at least from eosinophils, basophils and immature granulocytes stained with Astrazon Yellow 3G and Neutral Red is emitted. As this light source 1, an argon ion laser or a mercury arc lamp capable of emitting light of 400 to 520 nm in wavelength may be preferably used. The light from the light source is condensed in a flow area 20 of particles by a lens 2 in the form of a flat circle and a particle 13 (cell etc.) passing therethrough is irradiated therewith. Thus forward scattered light 21 is emitted forward from the particle 13, while red fluorescence 22, green fluorescence 23 and side scattered light 24 are emitted sideways from the same.

The particles are discharged from a nozzle 17, enveloped in a sheath fluid supplied from a sheath fluid inlet 14, and then form a sheath flow in a flow cell.

Direct light is removed from the forward scattered light 21 with a beam stopper 5 and the scattered light is transported to a light detection unit 6 via a condenser lens 4. On the other hand, the lights 22, 23 and 24 emitted sideway are transported to light detection units via a condenser lens 3. The side scattered light 24 is reflected upon a dichroic mirror 10 and then transported to a light detection unit 7. The red fluorescence 22 is reflected upon a dichroic mirror 11 and transported to a light detection unit 8. The green fluorescence 23 passes through a dichroic mirror 11 and is transported to a light detection unit 9. Then the lights transported to the light detection units 6, 7, 8 and 9 are respectively converted into electric signals which are amplified in a signal treatment unit 15 and analyzed in an analysis unit 16.

The term "forward scattered light" to be used herein means scattered light emitted from a cell passing through the detection unit at a narrow angle of almost 0° based on the emission axis of the light source.

The term "side scattered light" as used herein means scattered light emitted from a cell to be detected at an angle of almost 90° based on the emission axis of the light source. The term "red fluorescence" means fluorescence of a wavelength of 560 nm and above from among those emitted in all directions from a cell. Fluorescence at almost 0° or 90° from the emission axis of a light source can be condensed with a usual flow cytometer.

The term "green fluorescence" means fluorescence of a wavelength around 520 to 560 nm from among those emitted in all directions from a cell. Fluorescence at almost 0° or 90° from the emission axis of a light source can be condensed with a usual flow cytometer.

Now, the treatment steps of the present invention will be described by reference to particular examples. Reagents used in these examples were prepared from marketed chemical materials of reagent grade. A flow cytometer of a construction similar to the one shown in FIG. 1 was used for evaluation.

EXAMPLE 1

In this Example, a method for preparing a specimen to be used in order to separate leukocytes into at least three subpopulations (namely, one comprising eosinophils, one comprising basophils and one comprising immature granulocytes) by measuring three optical factors including red fluorescence, green fluorescence and side scattered light is shown.

| Composition Example 1: | |
|---|---|
| Astrazon Yellow 3G | 300 mg |
| Neutral Red | 20 mg |
| TRIS | 3.6 g |
| NaOH | sufficient for adjusting pH = 9.0 |
| NaCl | sufficient for adjusting osmotic pressure = 280 mOsm/kg |
| purified water | 1 l. |

Figure 22:
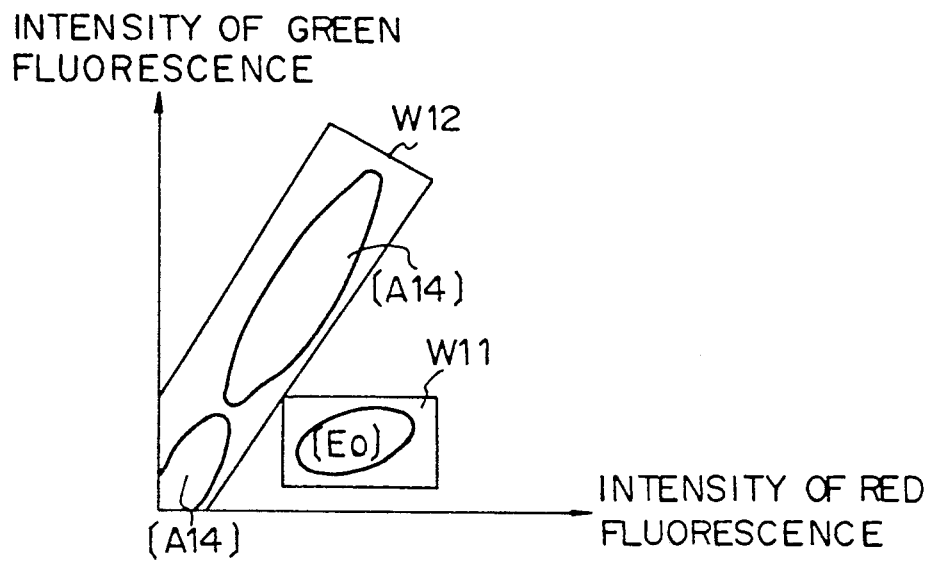
FIG. 22 is a scattergram wherein the intensity of red fluorescence and the intensity of green fluorescence of the specimen obtained in Example 1 are referred to as the coordinate axes.
Figure 23:
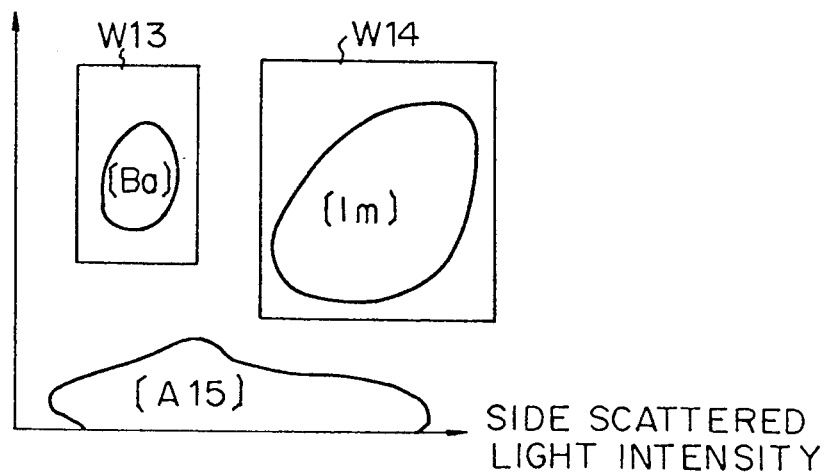
FIG. 23 is a scattergram wherein the side scattered light intensity and the intensity of red or green fluorescence of the data of the subpopulation [A14] in FIG. 22 are referred to as the coordinate axes.

0.95 ml of a reagent of the above Composition Example 1 was mixed with 0.05 ml of peripheral blood and then allowed to stand for 10 seconds or longer. Thus a specimen to be assayed was obtained. Leukocytes were classified and counted by measuring the red fluorescence, green fluorescence and side scattered light of each cell with a flow cytometer and then analyzing the obtained data by, for example, the following method. Namely, a scattergram was formed by referring to the intensity of red fluorescence and that of green fluorescence as the coordinate axes, as shown in FIG. 22. Thus at least two subpopulations including one comprising eosinophils [Eo] and another comprising other blood corpuscles [A14] were obtained. Then the eosinophils alone were gated within a window 11 [W11] and counted. Next, the data of the blood corpuscles other than eosinophils were gated with a window 12 [W12] and a scattergram was formed by referring the side scattered light intensity and the intensity of red or green fluorescence to as the coordinate axes as shown in FIG. 23. Thus leukocytes were divided into three subpopulations involving one comprising basophils [Ba], one comprising immature granulocytes [Im] and one comprising other blood corpuscles [A15]. The basophils and immature granulocytes were gated respectively with a window 13 [W13] and another window 14 [W14], followed by counting.

The term "window" as used herein means a specific area on a scattergram, while the term "gating" as used herein means a procedure for exclusively taking out the data of the area defined with a window. Further, the data in a window can be counted by delineated a specific area with the window.

EXAMPLE 2

In this Example, a method, which involves a first step for eliminating influences of erythrocytes, for preparing a specimen to be used in order to separate leukocytes into at least six subpopulations by measuring three optical factors including red fluorescence, green fluorescence and side scattered light is shown.

| Composition Example 2: | |
| --- | --- |
| First reagent solution: | |
| Astrazon Yellow 3G | 300 mg |
| Neutral Red | 20 mg |
| citric acid monohydrate | 2.10 g (pH 2.62) |
| purified water | 1 l |
| Second reagent solution: | |
| TRIS | 36.3 g |
| NaCl | 58.4 g |
| NaOH | 18.8 g |
| purified water | 1 l |

Figure 24:
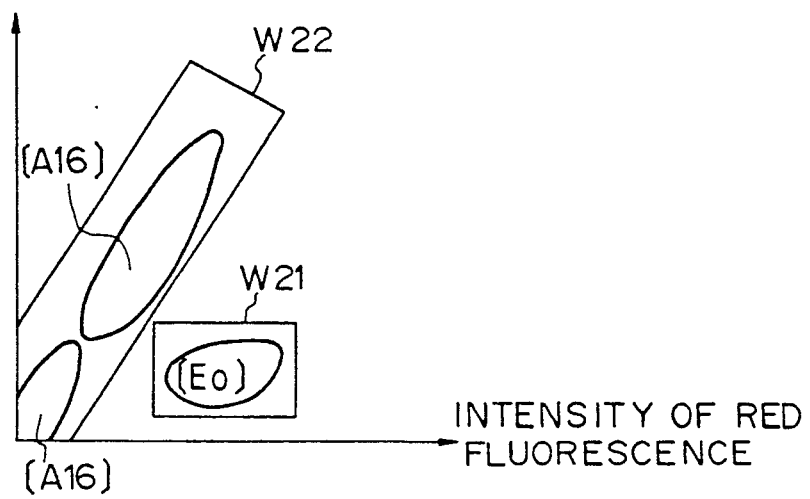
FIG. 24 is a scattergram wherein the intensity of red fluorescence and the intensity of green fluorescence of the specimen obtained in Example 2 are referred to as the coordinate axes.
Figure 25:
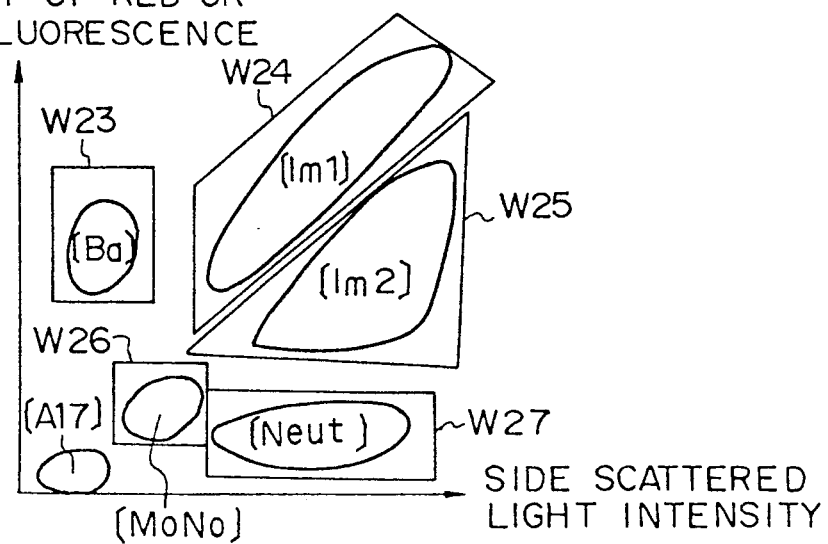
FIG. 25 is a scattergram wherein the side scattered light intensity and the intensity of red or green fluorescence of the data of the subpopulation [A16] in FIG. 24 are referred to as the coordinate axes.

0.90 ml of the first reagent solution of the above Composition Example 2 was mixed with 0.05 ml of peripheral blood and then allowed to incubate for 5 seconds or longer. Then 0.10 ml of the second reagent solution was further added thereto and the obtained mixture was allowed to incubate for an additional 10 seconds or longer. Thus specimen to be assayed was obtained. Leukocytes were classified and counted by measuring the red fluorescence, green fluorescence and side scattered light of each cell with a flow cytometer and then analyzing the obtained data by, for example, the following method. Namely, a scattergram was formed by referring to the intensity of red fluorescence and that of green fluorescence as the coordinate axes, as shown in FIG. 24. Thus at least two subpopulations including one comprising eosinophils [Eo] and another comprising other blood corpuscles [A16].were obtained. Then the eosinophils alone were gated within a window 21 [W21] and counted. Next, the data of the subpopulation [A16] comprising blood corpuscles other than eosinophils were gated with a window 22 [W22] and a scattergram was formed by referring the side scattered light intensity and the intensity of red or green fluorescence to as the coordinate axes, as FIG. 25 shows. Thus leukocytes were divided into six subpopulations, namely, one comprising monocytes [Mono], one comprising neutrophils [Neut], one comprising immature granulocytes 1 [Im1], another one comprising immature granulocytes 2 [Im2], one comprising basophils [Ba] and one comprising other blood corpuscles [A17].

The basophils, immature granulocytes 1, immature granulocytes 2, monocytes and neutrophils were gated respectively with a window 23 [W23], a window 24 [W24], a window 25 [W25], a window 26 [W26] and a window 27 [W27], followed by counting.

EXAMPLE 3

In this Example, a method, which involves a first step for eliminating influences of erythrocytes, for preparing a specimen to be used in order to separate leukocytes into at least seven subpopulations by measuring four optical factors including red fluorescence, green fluorescence, side scattered light and forward scattered light is shown.

0.90 ml of the first reagent solution of the above Composition Example 2 was mixed with 0.05 ml of peripheral blood and then allowed to incubate for 5 seconds or longer. Next, 0.10 ml of the second reagent solution was further added thereto and the obtained mixture was allowed to incubate for 10 seconds or longer. Then four optical factors (red fluorescence, green fluorescence, side scattered light and forward scattered light) of each cell were measured with a flow cytometer.

Figure 26:
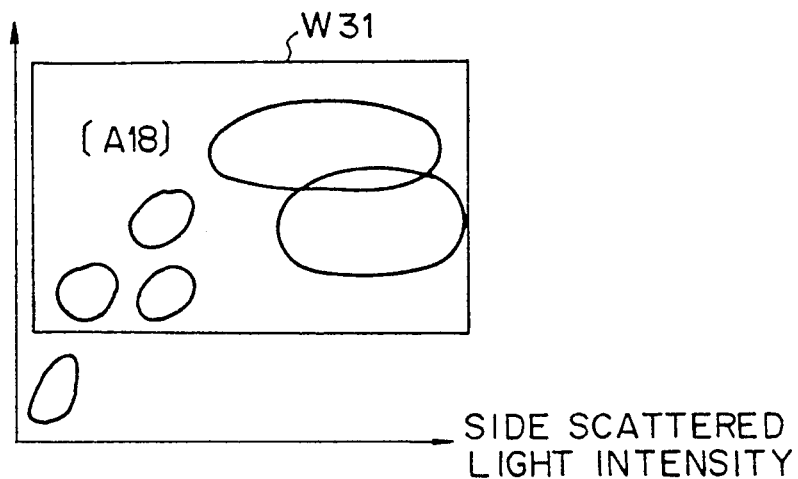
FIG. 26 is a scattergram wherein the forward scattered light intensity and the side scattered light intensity of the specimen obtained in Example 3 are referred to as the coordinate axes.
Figure 27:
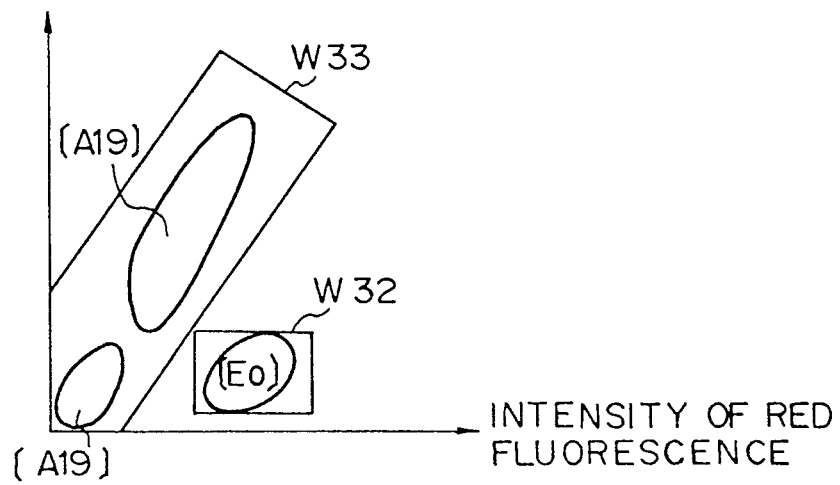
FIG. 27 is a scattergram wherein the intensity of red fluorescence and the intensity of green fluorescence of the data of the subpopulation [A18] in FIG. 26 are referred to as the coordinate axes.
Figure 28:
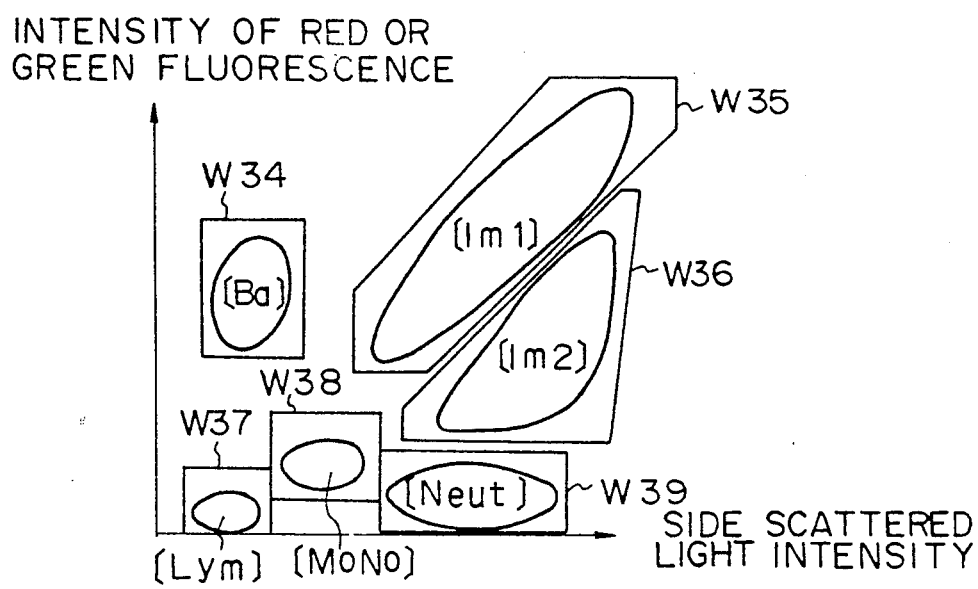
FIG. 28 is a scattergram wherein the side scattered light intensity and the intensity of red or green fluorescence of the data of the subpopulation [A19] in FIG. 27 are referred to as the coordinate axes.

First, a scattergram was formed by referring to the forward scattered light and the side scattered light as the coordinate axes, as shown in FIG. 26. Then a population comprising leukocytes alone [A18] was gated with a window 31 [W31] to thereby count the whole number of leukocytes. Next, a scattergram was formed by referring the intensity of red fluorescence and that of green fluorescence to as the coordinate axes, as shown in FIG. 27. Then eosinophils [Eo] alone were counted with a window 32 [W32]. Next, the data of the leukocytes other than eosinophils were gated with a window 33 [W33] and a scattergram was formed by referring the side scattered light intensity and the intensity of red or green fluorescence to as the coordinate axes, as shown in FIG. 28. Thus leukocytes were divided into six subpopulations involving one comprising lymphocytes [Lym], one comprising monocytes [Mono], one comprising neutrophils [Neut], one comprising immature granulocytes 1 [Im1], another one comprising immature granulocytes 2 [Im2] and one comprising basophils [Ba]. The basophils, immature granulocytes 1, immature granulocytes 2, lymphocytes, monocytes, and neutrophils were gated respectively with a window 34 [W34], a window 35 [W35], a window 36 [W36], a window 37 [W37], a window 38 [W38] and a window 39 [W39], followed by counting.

EXAMPLE 4

In this Example, a method, which involves a second step for eliminating influences of erythrocytes, for preparing a specimen to be used in order to separate leukocytes into at least six subpopulations by measuring three optical factors including red fluorescence, green fluorescence and side scattered light is shown.

| Composition Example 3: | |
| --- | --- |
| Astrazon Yellow 3G | 300 mg |

-continued

| Composition Example 3: | |
|---|---|
| Neutral Red | 20 mg |
| Astrazon Orange R | 300 mg |
| TRIS | 3.6 g |
| NaOH | sufficient for adjusting pH = 9.0 |
| NaCl | sufficient for adjusting osmotic pressure = 280 mOsm/kg |
| purified water | 1 l |

Figure 29:
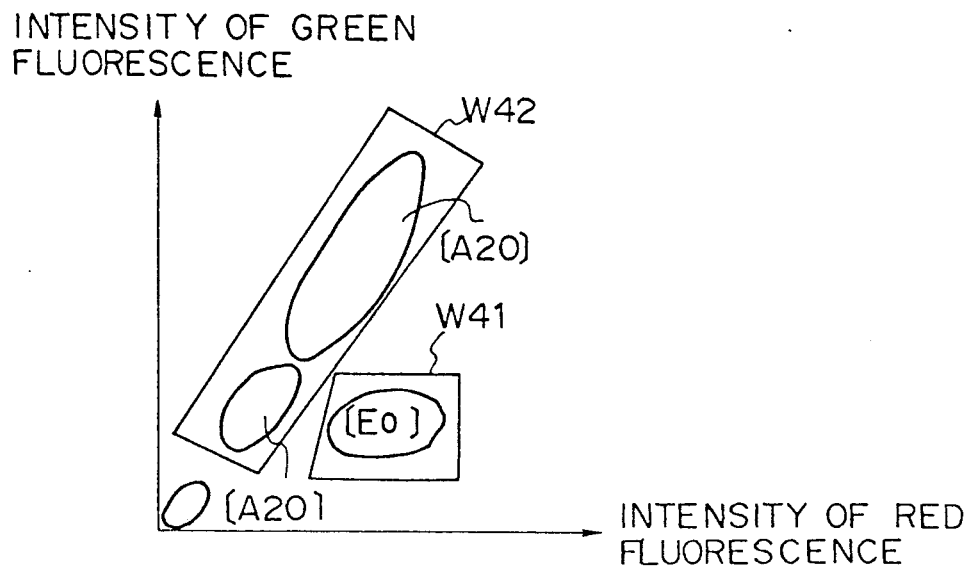
FIG. 29 is a scattergram wherein the intensity of red fluorescence and the intensity of green fluorescence of the specimen obtained in Example 4 are referred to as the coordinate axes.
Figure 30:
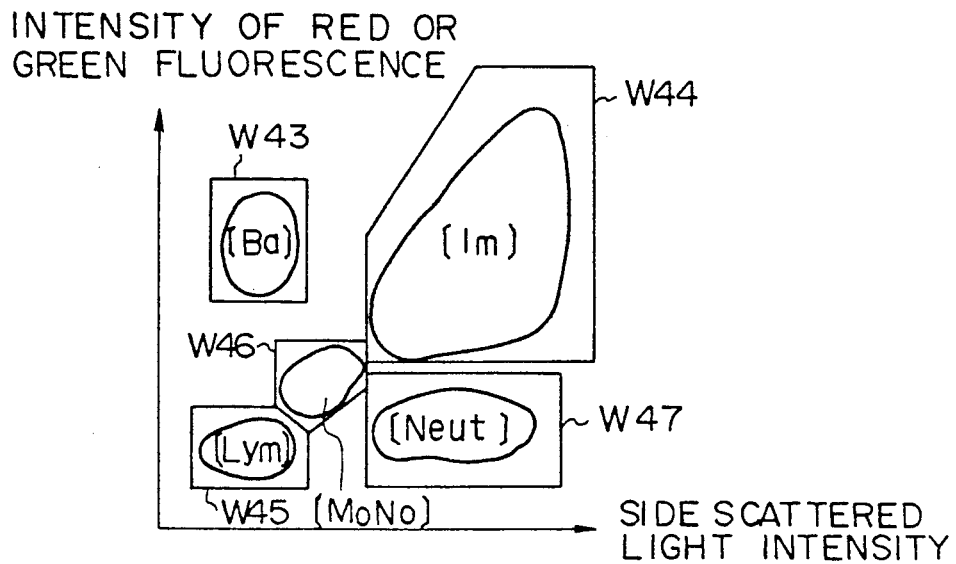
FIG. 30 is a scattergram wherein the side scattered light intensity and the intensity of red or green fluorescence of the data of the subpopulation [A20] in FIG. 29 are referred to as the coordinate axes.

0.95 ml of a reagent of the above Composition Example 3 was mixed with 0.05 ml of peripheral blood and then allowed to incubate for 10 seconds or longer. Thus a specimen to be assayed was obtained. Leukocytes were classified and counted by measuring the red fluorescence, green fluorescence and side scattered light of each cell with a flow cytometer and then analyzing the obtained data by, for example, the following method. Namely, a scattergram was formed by referring to the intensity of red fluorescence and that of green fluorescence as the coordinate axes, as shown in FIG. 29. Then eosinophils alone were gated within a window 41 [W41] and counted. Next, the data of the population [A20] of leukocytes other than eosinophils were gated with a window 42 [W42] and a scattergram was formed by referring the side scattered light intensity and the intensity of red or green fluorescence to as the coordinate axes. Thus basophils, immature granulocytes, lymphocytes, monocytes and neutrophils were classified respectively with a window 43 [W43], a window 44 [W44], a window 45 [W45], a window 46 [w46] and a window 47 [W47], followed by counting.

EXAMPLE 5

In this Example, a method, which involves a first step and a second step for eliminating influences of erythrocytes, for preparing a specimen to be used in order to separate leukocytes into at least seven subpopulations by measuring three optical factors including red fluorescence, green fluorescence and side scattered light is shown.

| Composition Example 4: | |
|---|---|
| First reagent solution: | |
| Astrazon Yellow 3G | 800 mg |
| Neutral Red | 20 mg |
| Astrazon Orange R | 300 mg |
| citric acid monohydrate | 2.10 g (pH 2.62) |
| purified water | 1 l |
| Second reagent solution: | |
| TRIS | 36.3 g |
| NaCl | 58.4 g |
| NaOH | 18.8 g |
| purified water | 1 l |

Figure 31:
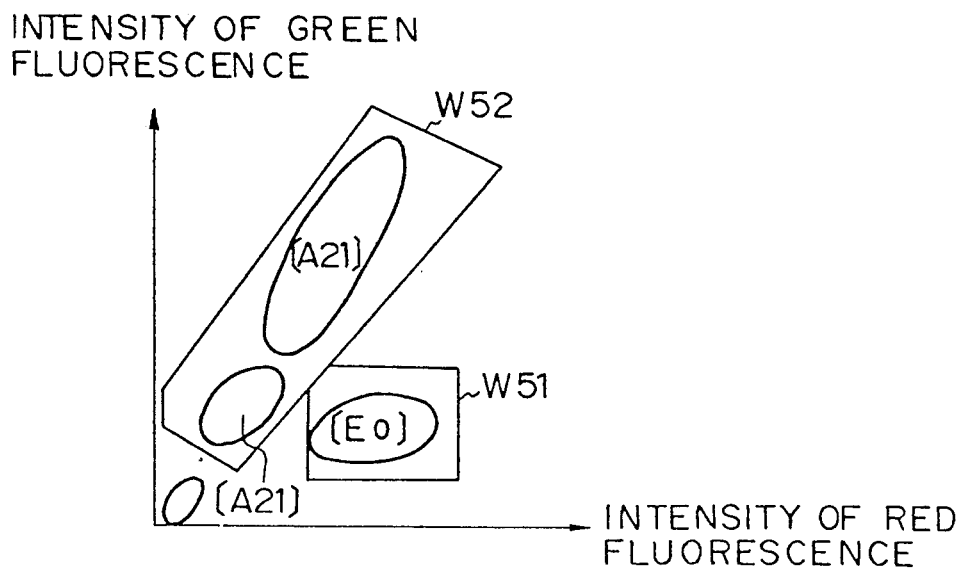
FIG. 31 is a scattergram wherein the intensity of red fluorescence and the intensity of green fluorescence of the specimen obtained in Example 5 are referred to as the coordinate axes.
Figure 32:
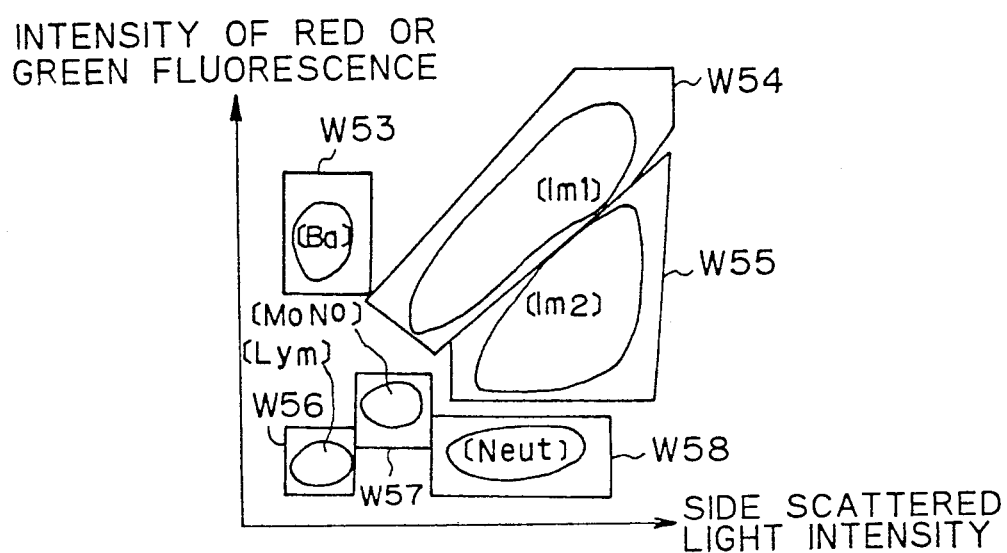
FIG. 32 is a scattergram wherein the side scattered light intensity and the intensity of red or green fluorescence of the data of the subpopulation [A21] in FIG. 31 are referred to as the coordinate axes.

0.90 ml of the first reagent solution of the above Composition Example 4 was mixed with 0.05 ml of peripheral blood and then allowed to incubate for 5 seconds or longer. Then 0.10 ml of the second reagent solution was further added thereto and the obtained mixture was allowed to incubate for an additional 10 seconds or longer. Thus a specimen to be assayed was obtained. Leukocytes were classified and counted by measuring the red fluorescence, green fluorescence and side scattered light of each cell with a flow cytometer and then analyzing the obtained data by, for example, the following method. Namely, a scattergram was formed by referring to the intensity of red fluorescence and that of green fluorescence as the coordinate axes, as shown in FIG. 31. Then eosinophils alone were gated within a window 51 [W51] and counted. Next, the data of a subpopulation [A21] comprising leukocytes other than eosinophils were gated with a window 52 [W52] and a scattergram was formed by referring to the side scattered light intensity and the intensity of red or green fluorescence as the coordinate axes, as FIG. 32 shows. Thus basophils [Ba], immature granulocytes 1 [Im1], immature granulocytes 2 [Im2], lymphocytes [Lym], monocytes [Mono] and neutrophils [Neut] were gated respectively with a window 53 [W53], a window 54 [W54], a window 55 [W55], a window 56 [W56], a window 57 [W57] and a window 58 [W58], followed by counting.

1. The present invention provides a method for preparing a specimen usable in flow cytometry whereby immature granulocytes can be separated from other leukocytes by specifically fluorochrome-staining immature granulocytes with Astrazon Yellow 3G and Neutral red. Thus it becomes possible to classify and count immature granulocytes, which cannot be achieved by any known methods.

2. When the above-mentioned method is combined with a step for eliminating influences of erythrocytes, furthermore, the classification and counting of leukocytes, including the classification and counting of immature granulocytes, can be achieved by assaying a single specimen. Leukocytes can be classified into at least seven subpopulations and counted by appropriately combining suitable methods for preparing a specimen.

What is claimed is:

1. A method for classifying and counting leukocytes into at least three groups including immature granulocytes by assaying a single specimen with a flow cytometer, which comprises the following steps:
   (1) a step for adjusting a pH value of a hematological sample to a level suitable for staining;
   (2) a step for staining leukocytes contained in said hematological sample with a mixture of at least two dyes specified as follows:
      i) Astrazon Yellow 3G capable of staining at least basophils and immature granulocytes; and
      ii) Neutral Red capable of staining at least eosinophils; and
   (3) a step for counting and classifying the leucocyte with a flow cytometer.

2. A method for classifying and counting leukocytes into at least six groups including immature granulocytes by assaying a single specimen with a flow cytometer, which comprises the following steps:
   (1) a step for eliminating influences of erythrocytes from a hematological sample without changing the leukocytes morphologically;
   (2) a step for adjusting a pH value of said hematological sample to a level suitable for staining;
   (3) a step for staining leukocytes contained in said hematological sample with a mixture of at least two dyes specified as follows:
      i) Astrazon Yellow 3G capable of staining at least basophils and immature granulocytes; and
      ii) Neutral Red capable of staining at least eosinophils; and
   (4) a step for counting and classifying leucocyte with a flow cytometer.

3. A method according to claim 2, wherein said step for eliminating influences of erythrocytes from said hematological sample without changing leukocytes morphologically is performed by reducing said erythrocytes into fragments and comprises the steps of:
  (1) fragmentizing said erythrocytes in said hematological sample by adding a first hypotonic aqueous solution to the hematological sample to form a resulting combined solution, said first hypotonic aqueous solution comprising a buffer for maintaining the pH value of the resulting combined solution acidic to said hematological sample; and
  (2) adding a second aqueous solution comprising an osmolarity compensating agent for maintaining the morphology of leukocytes and a buffer for neutralizing the acid in the resulting combined solution of the above (1);
to thereby classify the leukocytes in the hematological sample into six groups respectively comprising monocytes, neutrophils, eosinophils, basophils, immature granulocytes 1 and immature granulocytes 2, followed by counting.

4. A method according to claim 2, wherein said step for eliminating influences of erythrocytes in said hematological sample without changing leukocytes morphologically comprises:
  a step for staining the leukocytes in the hematological sample with at least one dye capable of staining at least either nuclei or cytoplasm of leukocytes in order to separate the leukocytes from other blood corpuscles depending on difference in the intensity of fluorescence at the time of measurement with a flow cytometer;
to thereby classify the leukocytes in the hematological sample into six groups respectively comprising lymphocytes, monocytes, neutrophils, eosinophils, basophils and immature granulocytes, followed by counting.

5. A method according to claim 4, wherein said dye capable of staining at least nuclei or cytoplasm of leukocytes is at least one dye selected from a group consisting of the following dyes:
  (1) Astrazon Orange R
  (2) Astra Violet
  (3) Rhodamine 6G
  (4) Rhodamine 19
  (5) Rhodamine B
  (6) Rhodamine 3GO
  (7) Pyronine B
  (8) Cyanosine
  (9) 3,3'-dimethylthiocarbocyanine iodide
  (10) 3,3'-diethylthiocarbocyanine iodide
  (11) 3,3'-dipropyloxacarbocyanine iodide
  (12) 3,3'-dihexyloxacarbocyanine iodide
  (13) 3,6-bis(dimethylamino)-10-dodecylacridinium bromide
  (14) 7-benzylamino-4-nitrobenzoxadiazole
  (15) 7-fluoro-4-nitrobenzoxadiazole
  (16) Astrazon Red 6B.

6. A method according to claim 2, wherein said step for eliminating influences of erythrocytes from said hematological sample without changing leukocytes morphologically comprises the steps of:
  (1) fragmentizing erythrocytes in said hematological sample by adding a first hypotonic aqueous solution to the hematological sample to form a resulting combined solution, said first hypotonic aqueous solution comprising a buffer for maintaining the pH value of the resulting combined solution acidic to said hematological sample;
  (2) adding a second aqueous solution comprising an osmolarity compensating agent for maintaining the morphology of leukocytes and a buffer for neutralizing the acid in the resulting combined solution of the above (1); and
  (3) staining leukocytes in the hematological sample with at least one dye capable of staining at least either of nuclei or cytoplasm of leukocytes to thereby separate the leukocytes from other blood corpuscles depending on the intensity of fluorescence at the time of measurement with a flow cytometer; to thereby divide the leukocytes in the hematological sample into seven groups respectively comprising lymphocytes, monocytes, neutrophils, eosinophils, basophils, immature granulocytes 1 and immature granulocytes 2, followed by counting.

7. A method according to claim 6, wherein said dye capable of staining at least nuclei or cytoplasm of leukocytes is at least one dye selected from a group consisting of the following dyes:
  (1) Astrazon Orange R
  (2) Astra Violet
  (3) Rhodamine 6G
  (4) Rhodamine 19
  (5) Rhodamine B
  (6) Rhodamine 3GO
  (7) Pyronine B
  (8) Cyanosine
  (9) 3,3'-dimethylthiocarbocyanine iodide
  (10) 3,3'-diethylthiocarbocyanine iodide
  (11) 3,3'-dipropyloxacarbocyanine iodide
  (12) 3,3'-dihexyloxacarbocyanine iodide
  (13) 3,6-bis(dimethylamino)-10-dodecylacridinium bromide
  (14) 7-benzylamino-4-nitrobenzoxadiazole
  (15) 7-fluoro-4-nitrobenzoxadiazole
  (16) Astrazon Red 6B.

* * * * *

UNITED STATES PATENT AND TRADEMARK OFFICE
CERTIFICATE OF CORRECTION

PATENT NO. : 5,308,772
DATED : May 3, 1994
INVENTOR(S) : Takashi Sakata et al.

It is certified that error appears in the above-identified patent and that said Letters Patent is hereby corrected as shown below:

On the title page, insert: [56] References Cited, U.S. Patent Documents, insert the following:

--4,581,223  4/1986  Kass................424/3--

References Cited, Foreign Patent Documents, insert the following:

--0229512  7/1987  European Patent Office
  0343380  11/1989  European Patent Office
  0268766  6/1988  European Patent Office--.

Column 7, line 53, delete "thus" and insert --Thus--.

Column 14, line 30, insert -- $\Theta$ -- between the " $R_i$ " symbols.

Column 23, line 45, delete "800 mg" and insert --300 mg--.

Signed and Sealed this

Fourth Day of July, 1995

Attest:

BRUCE LEHMAN

Attesting Officer    Commissioner of Patents and Trademarks